United States Patent
Urbanski et al.

(10) Patent No.: US 10,493,259 B2
(45) Date of Patent: Dec. 3, 2019

(54) MEDICAL APPARATUS FOR FLUID COMMUNICATION

(71) Applicant: Baylis Medical Company Inc., Mississauga (CA)

(72) Inventors: John Paul Urbanski, Toronto (CA); Krishan Shah, Mississauga (CA); Gareth Davies, Toronto (CA); Mahmood Mirza, North York (CA); Naheed Visram, Epsom (GB); Amanda Hartley, Caledon (CA)

(73) Assignee: Baylis Medical Company Inc., Montreal, Quebec (CA)

( * ) Notice: Subject to any disclaimer, the term of this patent is extended or adjusted under 35 U.S.C. 154(b) by 982 days.

(21) Appl. No.: 14/222,909

(22) Filed: Mar. 24, 2014

(65) Prior Publication Data
US 2014/0206987 A1    Jul. 24, 2014

Related U.S. Application Data

(60) Continuation-in-part of application No. 13/468,939, filed on May 10, 2012, now Pat. No. 8,679,107.
(Continued)

(51) Int. Cl.
*A61B 18/18* (2006.01)
*A61M 39/08* (2006.01)
(Continued)

(52) U.S. Cl.
CPC .............. *A61M 39/08* (2013.01); *A61B 5/065* (2013.01); *A61B 5/103* (2013.01);
(Continued)

(58) Field of Classification Search
CPC ...... A61B 18/1492; A61B 2017/00247; A61B 2018/00083; A61B 2018/00351;
(Continued)

(56) References Cited

U.S. PATENT DOCUMENTS

| 4,129,129 A | 12/1978 | Amrine |
| 4,639,252 A | 1/1987 | Kelly et al. |
(Continued)

FOREIGN PATENT DOCUMENTS

| CA | WO2004/064657 A2 | 8/2004 |
| EP | 1474203 | 11/2004 |
(Continued)

OTHER PUBLICATIONS

Entire Prosecution History of U.S. Appl. No. 13/468,939 from May 10, 2012 to Mar. 5, 2014.
(Continued)

*Primary Examiner* — Michael F Peffley
*Assistant Examiner* — Amanda L Zink
(74) *Attorney, Agent, or Firm* — Glenn Arnold; Nir Litshitz; Vincent Man

(57) ABSTRACT

This disclosure describes embodiments of a kit and its constituent components which together form an apparatus in which fluid communication between a medical device's lumen and the surrounding environment is provided by a conduit cooperatively defined by the medical device and a tubular member into which the device is inserted. The medical device and tubular member are configured to fit together such that an outer surface of the distal region of the medical device cooperates with an inner surface of the tubular member to define the conduit between the side-port of the medical device and a distal end of the tubular member. The conduit is operable to be used for injecting fluid, withdrawing fluid, and measuring pressure, for example. Methods of assembling and using the apparatus are described as well.

20 Claims, 16 Drawing Sheets

Related U.S. Application Data which is a division of application No. 11/905,447, filed on Oct. 1, 2007, now Pat. No. 8,192,425, application No. 14/222,909, which is a continuation-in-part of application No. 13/113,326, filed on May 23, 2011, now Pat. No. 9,597,146, which is a continuation-in-part of application No. 11/265,304, filed on Nov. 3, 2005, now Pat. No. 7,947,040, which is a continuation-in-part of application No. 10/666,301, filed on Sep. 19, 2003, now Pat. No. 7,048,733, and a continuation-in-part of application No. 10/760,479, filed on Jan. 21, 2004, now Pat. No. 7,270,662, and a continuation-in-part of application No. 10/666,288, filed on Sep. 19, 2003, now abandoned, which is a continuation-in-part of application No. 10/347,366, filed on Jan. 21, 2003, now Pat. No. 7,112,197, said application No. 11/265,304 is a continuation-in-part of application No. 10/347,366, filed on Jan. 21, 2003, now Pat. No. 7,112,197.

(60) Provisional application No. 60/884,285, filed on Jan. 10, 2007, provisional application No. 60/827,452, filed on Sep. 29, 2006, provisional application No. 60/522,753, filed on Nov. 3, 2004.

(51) Int. Cl.
| | |
|---|---|
| *A61B 5/06* | (2006.01) |
| *A61M 5/00* | (2006.01) |
| *A61B 5/103* | (2006.01) |
| *A61M 29/02* | (2006.01) |
| *A61B 18/14* | (2006.01) |
| *A61B 18/00* | (2006.01) |
| *A61B 17/00* | (2006.01) |
| *A61B 90/00* | (2016.01) |

(52) U.S. Cl.
CPC ......... *A61B 18/1492* (2013.01); *A61M 5/007* (2013.01); *A61M 29/02* (2013.01); *A61B 18/1482* (2013.01); *A61B 90/02* (2016.02); *A61B 2017/00247* (2013.01); *A61B 2018/00011* (2013.01); *A61B 2018/00083* (2013.01); *A61B 2018/00351* (2013.01); *A61B 2018/00839* (2013.01); *A61B 2090/064* (2016.02); *A61B 2090/0811* (2016.02); *A61B 2090/3966* (2016.02); *A61B 2090/3983* (2016.02); *A61B 2218/002* (2013.01); *Y10T 29/49826* (2015.01)

(58) Field of Classification Search
CPC ...... A61B 2090/064; A61B 2090/0811; A61B 2090/3966; A61B 2090/3983; A61B 2218/002; A61B 90/02; A61B 17/3476; A61B 18/1477; A61B 18/1482; A61B 2017/00862; A61B 2018/0001

See application file for complete search history.

(56) References Cited

U.S. PATENT DOCUMENTS

| | | | | |
|---|---|---|---|---|
| 4,863,441 | A | | 9/1989 | Lindsay et al. |
| 5,006,119 | A | * | 4/1991 | Acker ............... A61B 18/08 604/96.01 |
| 5,314,418 | A | * | 5/1994 | Takano ............... A61M 1/10 604/525 |
| 5,497,774 | A | * | 3/1996 | Swartz ............... A61M 25/0041 600/435 |
| 6,056,747 | A | * | 5/2000 | Saadat ............... A61B 18/14 606/42 |
| 6,193,715 | B1 | * | 2/2001 | Wrublewski ....... A61B 18/1402 604/22 |
| 6,302,898 | B1 | * | 10/2001 | Edwards .......... A61B 17/00491 606/213 |
| 6,562,031 | B2 | * | 5/2003 | Chandrasekaran ........................ A61B 18/1492 600/585 |
| 6,951,555 | B1 | | 10/2005 | Suresh et al. |
| 7,112,197 | B2 | | 9/2006 | Hartley et al. |
| 7,335,197 | B2 | * | 2/2008 | Sage ................. A61B 18/1492 606/41 |
| 7,682,360 | B2 | * | 3/2010 | Guerra ............ A61B 17/32002 606/167 |
| 8,192,425 | B2 | | 6/2012 | Mirza et al. |
| 8,257,323 | B2 | | 9/2012 | Joseph et al. |
| 8,388,549 | B2 | | 3/2013 | Paul et al. |
| 2005/0059966 | A1 | | 3/2005 | McClurken |
| 2005/0065507 | A1 | * | 3/2005 | Hartley ............. A61B 18/1492 606/41 |
| 2006/0142756 | A1 | * | 6/2006 | Davies .............. A61B 18/1492 606/45 |
| 2006/0241586 | A1 | | 10/2006 | Wilk |
| 2006/0264927 | A1 | * | 11/2006 | Ryan ............... A61B 17/32002 606/45 |
| 2007/0066975 | A1 | * | 3/2007 | Wong ................... A61B 18/24 606/45 |
| 2008/0086120 | A1 | | 4/2008 | Mirza |
| 2010/0191142 | A1 | | 7/2010 | Paul et al. |
| 2012/0232546 | A1 | | 9/2012 | Mirza |
| 2013/0184735 | A1 | | 7/2013 | Fischell |
| 2014/0206987 | A1 | | 7/2014 | Urbanski |

FOREIGN PATENT DOCUMENTS

| | | | |
|---|---|---|---|
| WO | 2013179103 | A1 | 12/2013 |
| WO | WO 2013/179103 | A1 | 12/2013 |

OTHER PUBLICATIONS

Patent Cooperation Treaty, International Search Report for International Application No. PCT/IB2015/052118, dated Jun. 26, 2015.
Patent Cooperation Treaty, Written Opinion of the International Search Authority for International Application No. PCT/IB2015/052118, dated Jun. 26, 2015.
Patent Cooperation Treaty, International Preliminary Report on Patentability, International Application No. PCT/IB2015/052118, dated Sep. 27, 2016.
First Office Action for Chinese Application, Application/Patent No. 2015800262435, Issue Serial No. 2018122001954460, dated Dec. 25, 2018.
Supplementary European Search Report, EP 15 76 8911, search completed on Nov. 1, 2017.
Search Opinion for Application No. 15 768 911.8.
Translation of above listed First Office Action for Chinese Application, Application/Patent No. 2015800262435, Issue Serial No. 2018122001954460, dated Dec. 25, 2018.

* cited by examiner

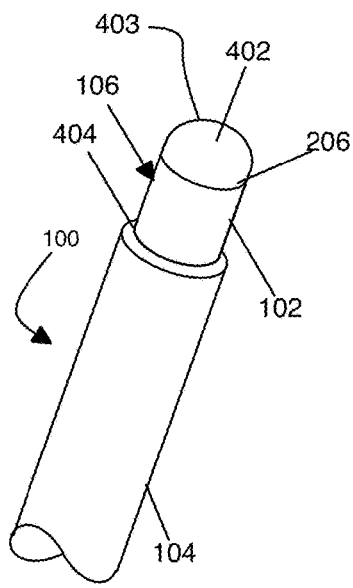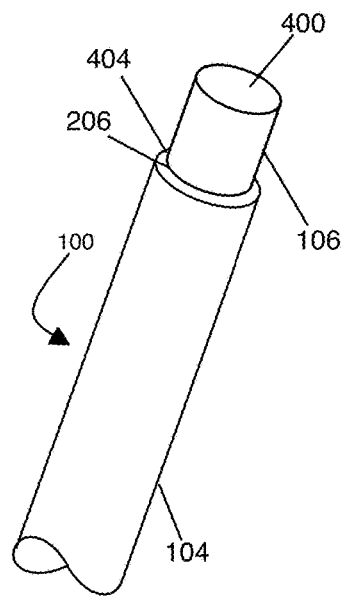
Fig. 3A    Fig. 3B
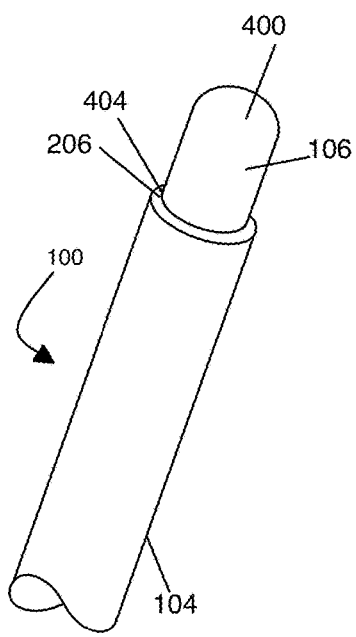
Fig. 3C

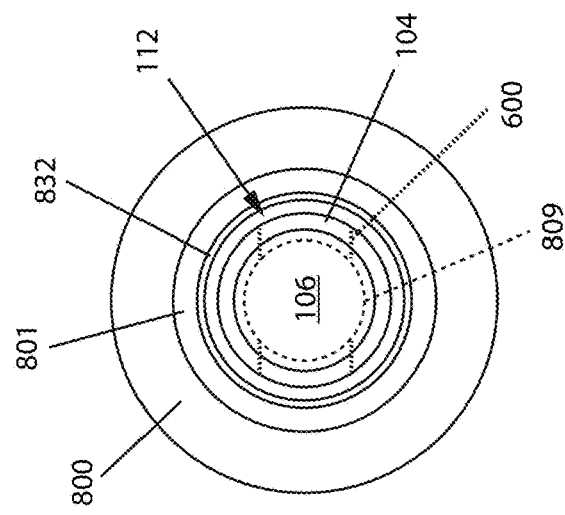
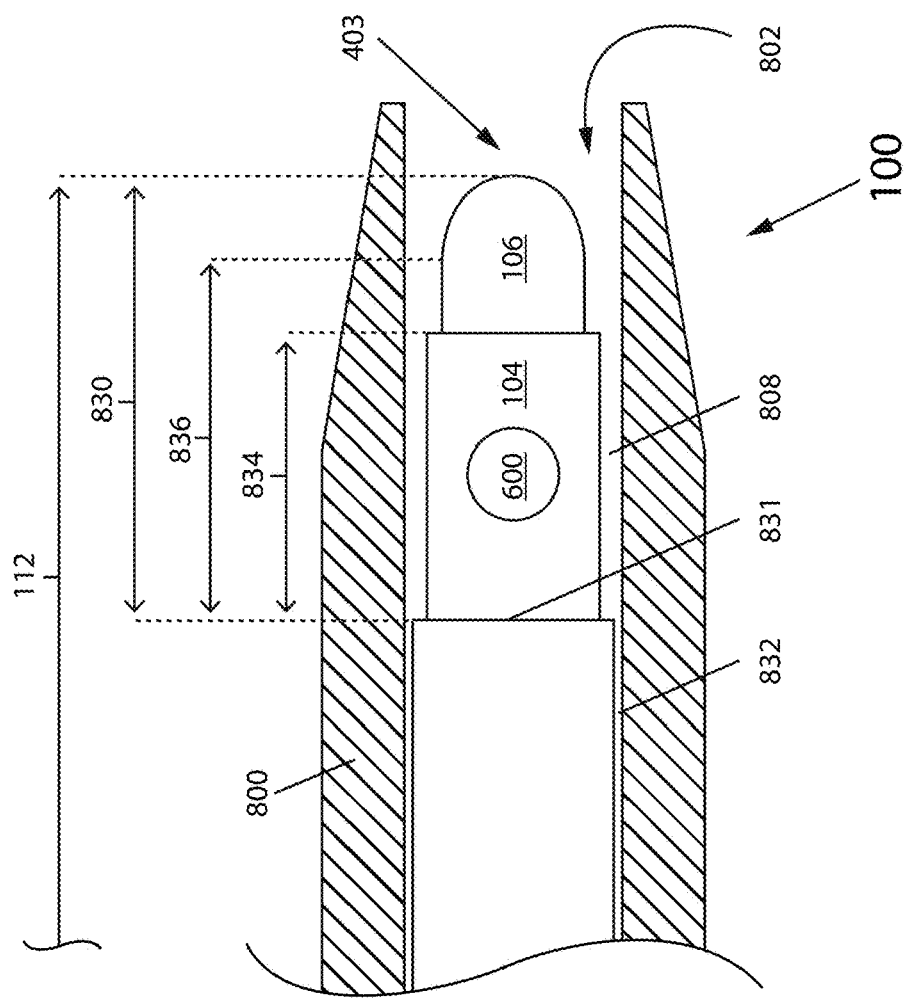
Fig. 4b
Fig. 4a

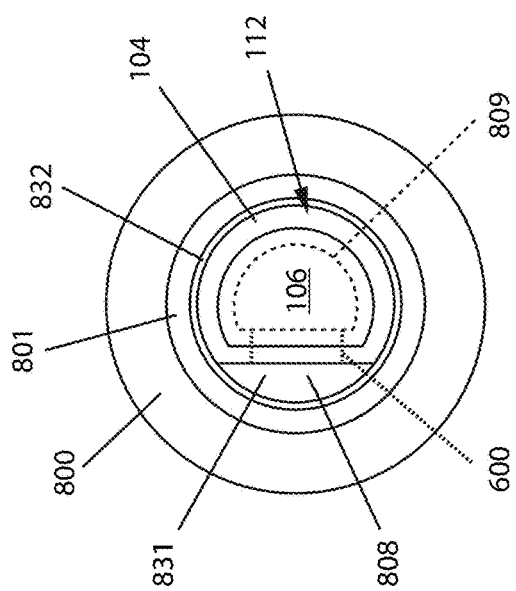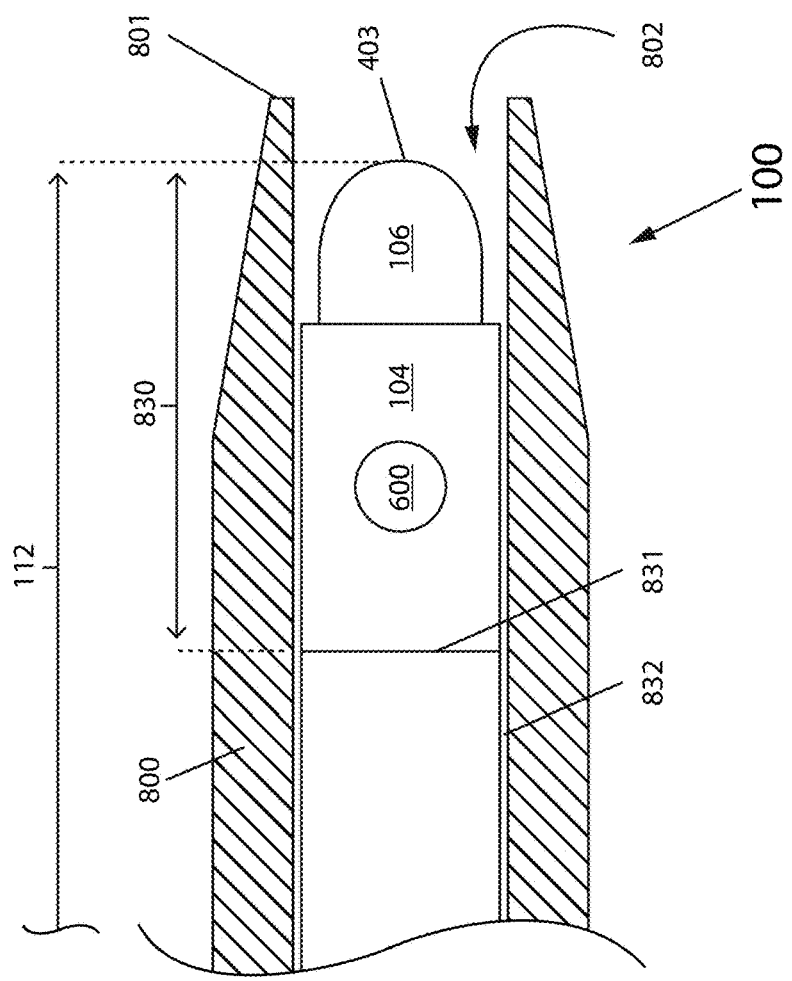

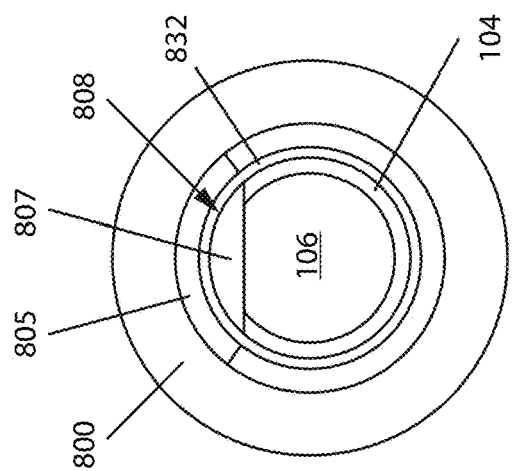
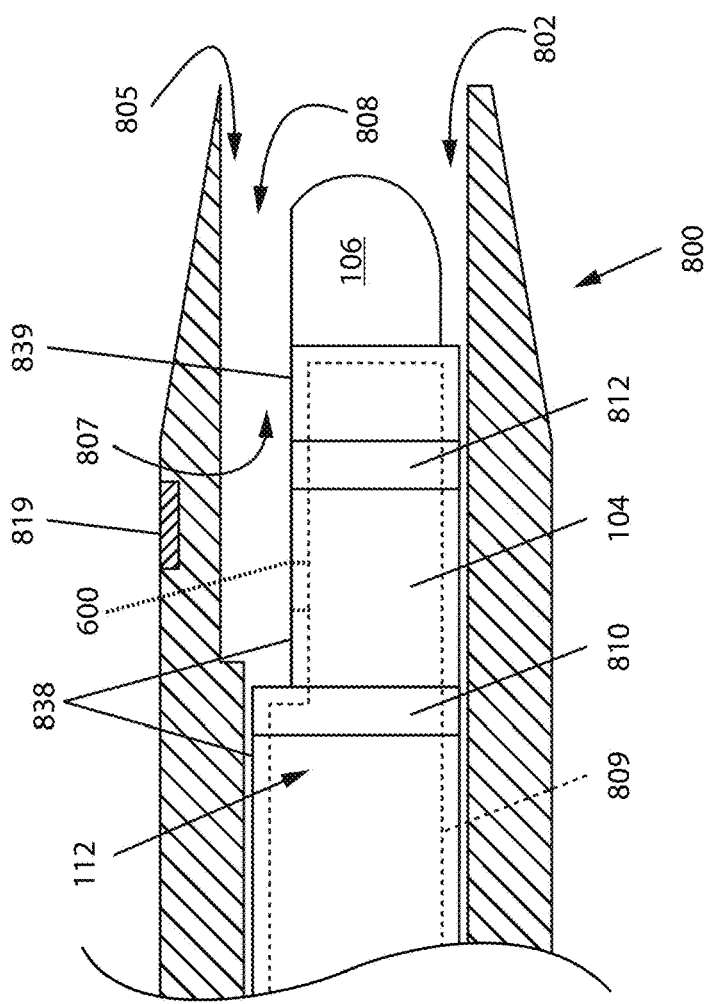

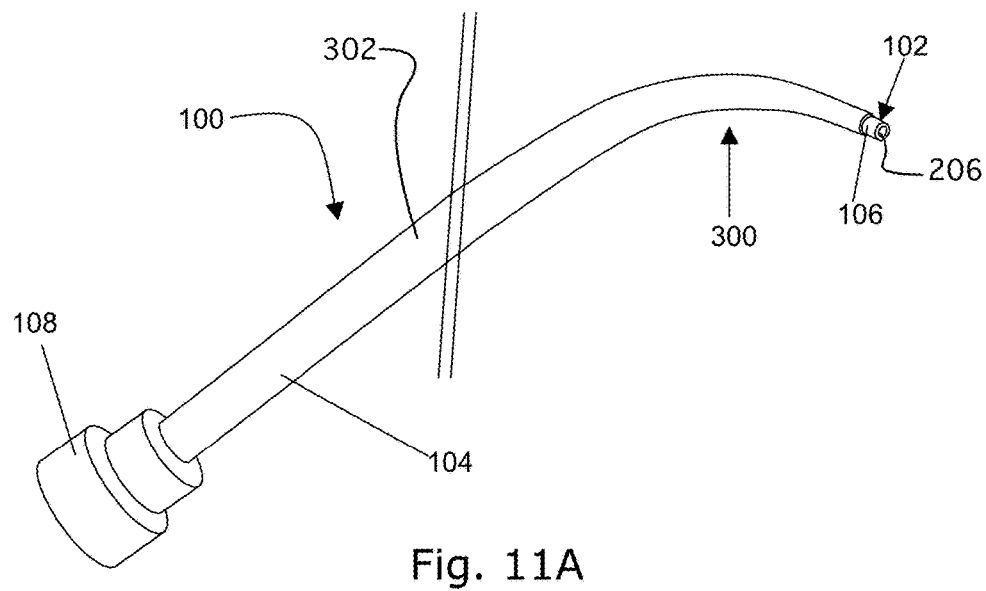
Fig. 11A
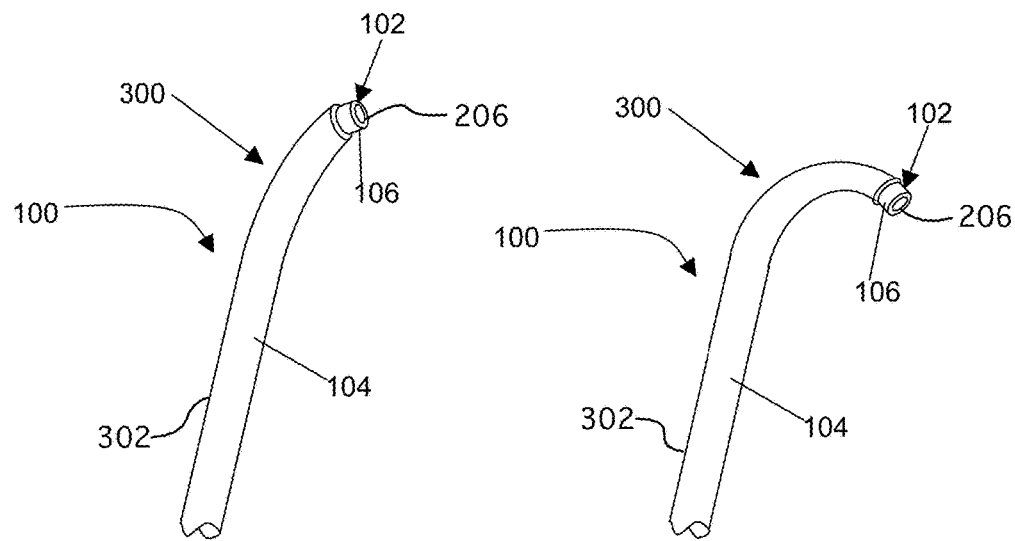
Fig. 11B
Fig. 11C

MEDICAL APPARATUS FOR FLUID COMMUNICATION

CROSS-REFERENCES TO RELATED APPLICATIONS

This application is a continuation-in-part of U.S. application Ser. No. 13/468,939, filed on May 10, 2012, now U.S. Pat. No. 8,679,939, which is a divisional application of, and claims priority from, U.S. application Ser. No. 11/905,447, filed on Oct. 1, 2007, now U.S. Pat. No. 8,192,425, which claims the benefit of: U.S. provisional application No. 60/827,452, filed on Sept. 29, 2006, and U.S. provisional application No. 60/884,285, filed on Jan. 10, 2007, all of which are incorporated by reference herein in their entirety. This application is also a continuation-in-part of U.S. application Ser. No. 13/113,326, filed May 23, 2011 now U.S. Pat. No. 9,597,146, which is a continuation-in-part of U.S. application Ser. No. 11/265,304, filed Nov. 3, 2005, now U.S. Pat. No. 7,947,040. U.S. application Ser. No. 11/265,304 is a continuation-in-part of U.S. application Ser. No. 10/666,301, filed Sep. 19, 2003, now issued as U.S. Pat. No. 7,048,733 and a continuation-in-part of U.S. application Ser. No. 10/760,479, filed Jan. 21, 2004, now issued as U.S. Pat. No. 7,270,662 and a continuation-in-part of U.S. application Ser. No. 10/666,288, filed Sep. 19, 2003, which is a continuation-in-part of U.S. application Ser. No. 10/347,366, filed Jan. 21, 2003, now issued as U.S. Pat. No. 7,112,197. U.S. application Ser. No. 11/265,304, now U.S. Pat. No. 7,947,040, claims priority from U.S. provisional application 60/522,753, filed Nov. 3, 2004. All of the aforementioned patents and applications are incorporated herein by reference in their entirety.

FIELD OF THE INVENTION

The present invention relates generally to methods and devices usable to deliver and withdraw fluids, and measure fluid pressure, within the body of a patient. More specifically, the present invention is concerned with medical devices with side apertures or side-ports.

SUMMARY OF THE DISCLOSURE

This disclosure describes embodiments of a kit and its constituent components which together form an apparatus in which fluid communication between a medical device's lumen and the surrounding environment is provided by a conduit cooperatively defined by the medical device and a tubular member into which the device is inserted. The medical device and tubular member are configured to fit together such that an outer surface of the distal region of the medical device cooperates with an inner surface of the tubular member to define the conduit between the side-port of the medical device and a distal end of the tubular member. The conduit is operable to be used for injecting fluid, withdrawing fluid, and measuring pressure, for example. Methods of assembling and using the apparatus are described as well.

In one broad aspect, embodiments of the present invention describe a method of establishing a conduit for fluid communication for a medical device, the method comprising the steps of: (a) inserting a medical device having at least one side-port into a tubular member; and (b) cooperatively defining a conduit for fluid communication by positioning the side-port of the medical device at a location of the tubular member at which a space exists between the side-port and an inner wall of the tubular member, the space forming a part of the conduit, the conduit extending at least between the side-port and a distal end of the tubular member.

As a feature of this broad aspect, some embodiments further comprise a step (c) of delivering a fluid through the side-port and distally through the distal end of the tubular member.

In another broad aspect, embodiments of the present invention include a medical device comprising an elongate member having a closed distal end, the elongate member defining a device lumen and at least one side-port in fluid communication with the device lumen, the elongate member defining a proximal portion and a distal portion, the distal portion extending from the at least one side-port to the distal end of the elongate member; the proximal portion defining a first outer diameter, the distal portion defining a second outer diameter, the first outer diameter being larger than the second outer diameter, the second outer diameter being substantially constant; and a distal tip comprising an electrode.

As a feature of this broad aspect, some embodiments further include: the elongate member comprising an electrically conductive material, a layer of insulation covering the electrically conductive material, and the electrically conductive material being electrically coupled to the electrode.

In another broad aspect, embodiments of the present invention include a dilator for use with a medical device, the dilator comprising: a tubular member defining a lumen and a distal end aperture in fluid communication therewith; a proximal region of the tubular member having a first inner diameter; a distal region of the tubular member having an increased diameter portion defining a second inner diameter, the increased diameter portion extending proximally from a distal end of the dilator; and the second inner diameter being substantially constant along the increased diameter portion and being greater than the first inner diameter.

In another broad aspect, embodiments of the present invention include a kit comprising: a tubular member defining a tubular member lumen and a distal end aperture in fluid communication therewith; and a medical device having a closed distal end, the medical device defining a device lumen and at least one side-port in fluid communication therewith, the medical device defining a distal portion extending from the at least one side-port to a distal end of the medical device; the medical device and tubular member being configured to cooperatively form a conduit between an outer surface of the distal portion and an inner surface of the tubular member when the medical device is inserted within the tubular member lumen, the conduit being formed at least between the side-port and the distal end aperture for enabling fluid communication between the side-port and an environment external to the distal end aperture.

In yet another broad aspect, embodiments of the present invention include an apparatus comprising: a tubular member defining a tubular member lumen and a distal end aperture in fluid communication therewith; a medical device located within the tubular member lumen, the medical device having a closed distal end, the medical device defining a device lumen and at least one side-port in fluid communication therewith, the medical device defining a distal portion extending from the at least one side-port to a distal end of the medical device; and a conduit defined between an outer surface of the distal portion of the medical device and an inner surface of the tubular member, the conduit being formed at least between the side-port and the distal end aperture for enabling fluid communication between the side-port and an environment external to the distal end aperture.

BRIEF DESCRIPTION OF THE DRAWINGS

In order that the invention may be readily understood, embodiments of the invention are illustrated by way of examples in the accompanying drawings, in which:

FIGS. 3A to 3D, in perspective views, illustrate various electrode configurations;

FIGS. 4A and 4B illustrate a partially cut away side view, and an end view, respectively, of a medical device and a tubular member in accordance with an embodiment of the present invention;

FIGS. 5A and 5B illustrate a partially cut away side view, and an end view, respectively, of a medical device and a tubular member in accordance with another embodiment of the present invention;

FIGS. 7A and 7B illustrate a partially cut away side view, and an end view, respectively, of a medical device and a tubular member in accordance with another embodiment of the present invention;

FIG. 11A, in a perspective view, illustrates a medical device in accordance with an yet another alternative embodiment of the present invention, the medical device including a curved section;

FIG. 11B, in a partial perspective view, illustrates a medical device in accordance with yet another alternative embodiment of the present invention, the medical device including an alternative curved section;

FIG. 11C, in a partial perspective view, illustrates a medical device in accordance with yet another alternative embodiment of the present invention, the medical device including another alternative curved section;

DETAILED DESCRIPTION

Figure 1:
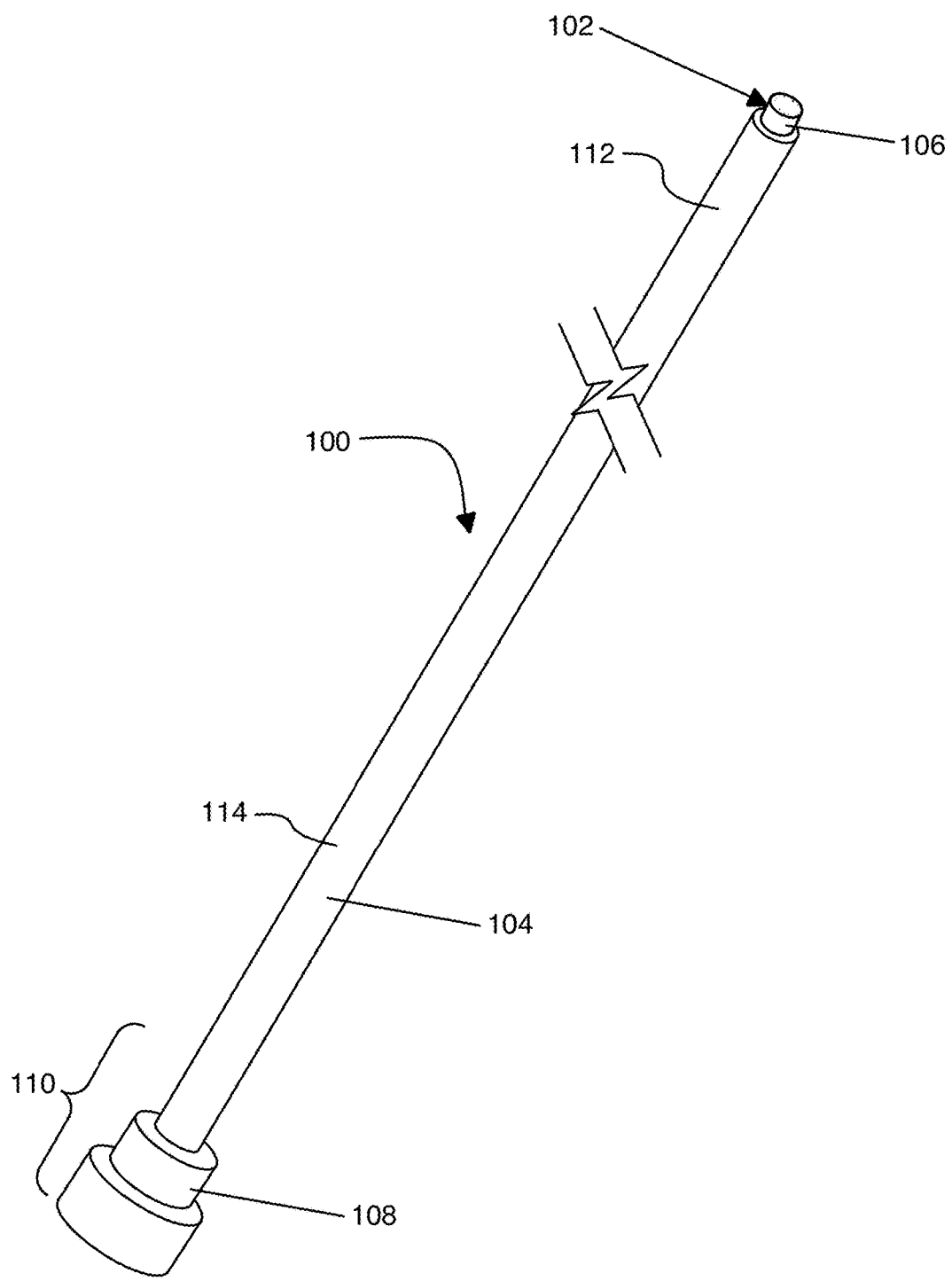
FIG. 1, in a perspective view, illustrates a medical device in accordance with an embodiment of the present invention.

Puncturing devices of various types are used to create punctures or channels through tissues. These devices include mechanical, electrical or optical puncturing means, for example. Typically, such devices are used in conjunction with tubular devices such as dilators or sheaths, through which the puncturing devices are inserted into a patient's body. In many applications, a user may desire to inject and/or withdraw fluid using the device prior to, during, or after puncturing.

The present inventors have discovered that attempting to inject and/or withdraw fluid while such puncturing devices are held within other tubular devices may require that excessive pressure and/or force (e.g. for suction or injection) be applied due to increased resistance to fluid flow as a result of a partial or total occlusion of apertures on the puncturing devices due to the dilator or sheath within which the device is inserted.

The present inventors have conceived of, and reduced to practice, embodiments of medical devices and tubular members, e.g. dilators, that are configured to cooperate to allow for more efficient fluid communication between a lumen of the medical device and an environment external to the dilator. This facilitates fluid transfer, pressure measurements and the like through the medical device even while the device is inserted within the tubular member.

Some embodiments of the present invention include a medical device with lateral apertures or side-ports which fits within a tubular member, wherein the medical device and tubular member are configured to cooperatively define a path or conduit for fluid communication between the lumen defined by the medical device and the environment outside the device and tubular member. In typical embodiments, the medical device and tubular member cooperatively form a conduit between an outer surface of the distal portion of the medical device and an inner surface of the tubular member when the medical device is inserted within the tubular member lumen, the conduit being formed at least between the side-port of the medical device and the distal end aperture of the tubular member. Embodiments of the present invention thus minimize or reduce any obstruction, blockage or partial blockage of side-ports of such medical devices by a dilator or any ancillary device through which the medical device is placed.

Embodiments of the present invention provide for improved efficiencies in fluid communication while avoiding the necessity of defining an open, or partially open, distal aperture (i.e. an aperture defined by a distal face/surface) in the medical device. This helps to mitigate a concern of cutting a plug of tissue (often referred to as 'coring' the tissue) when puncturing tissue using, for example, electrical energy with a circular, open-ended electrode. If an open-ended or open-faced ring electrode is used to cut tissue, a core (or plug) of tissue can be cut from the tissue and subsequently captured in the lumen of the device. The tissue core may then be released from the lumen by flushing, potentially leading to emboli and increasing the risk of a stroke or some other ischemic event. Embodiments of the present invention allow for fluid communication with an external environment without requiring an open distal end on the medical device, thereby obviating the concern of creating these embolic particles.

In addition, embodiments of the present invention allow for larger electrodes to be used for cutting or puncturing tissues, as described hereinbelow. Other advantages and benefits of embodiments of the present invention will be apparent to those of skill in the art in view of the instant disclosure.

With specific reference now to the drawings in detail, it is stressed that the particulars shown are by way of example and for purposes of illustrative discussion of embodiments of the present invention only. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein, the terms 'proximal' and 'distal' are defined with respect to the user. That is, the term 'proximal' refers to a part or portion closer to the user, and the term 'distal' refers to a part or portion further away from the user when the device is in use. Also, it should be noted that while, for clarity of explanation, the term tubular or tubular member is used to describe the members that enclose the disclosed medical devices, the term tubular member is intended to describe both circular and non-circular embodiments of the enclosing member. The term tubular member is used in this disclosure to describe dilators, sheaths, and other members that define a lumen for containing a medical device.

Referring to FIG. 1, there is shown a medical device 100 in accordance with an embodiment of the present invention. The medical device 100 is usable for creating a channel at a target location in a body of a patient. The medical device 100 includes a handle 110, a distal section 112 and a force transmitting section 114 extending between the distal section 112 and the handle 110. The distal section 112 defines a distal section length and includes an electrode 106 and an electrical insulator 104 extending from the electrode 106.

In typical embodiments of the invention, the medical device 100 includes an electrically conductive elongate member 102 having an electrical insulator 104 disposed thereon. The electrical insulator 104 substantially covers the entire outer surface of the elongate member 102 such that elongate member 102 is able to deliver energy from its proximal region to the electrode 106 at its distal region, without substantial leakage of energy along the length of the elongate member 102. The elongate member 102 defines a lumen 208 and at least one side-port 600 (shown, for example, in FIGS. 2A to 2D), which is in fluid communication with the lumen 208.

The one or more side-ports 600 are particularly useful in typical embodiments of medical device 100 wherein a lumen 208 of the elongate member 102 is not open to the surrounding environment via the distal end of the medical device 100 (i.e. wherein medical device 100 is a close-ended device), for example in the embodiments of FIGS. 3A to 3C, and 2E. In such embodiments, the lumen 208 extends substantially longitudinally through the force transmitting section 114 and through a section of the distal section 112 and terminates in the distal section 112 at a location substantially spaced apart from the distal tip 403, such that the distal tip 403 remains closed.

In embodiments comprising side-port(s) 600, the side-port(s) 600 allow for fluids to be injected into the surrounding environment from the lumen 208, and/or allow for pressure to be measured by providing a pressure transmitting lumen through medical device 100. In some examples, the side-port(s) 600 are formed radially through elongate member 102 and electrical insulator 104, thereby allowing for fluid communication between the surrounding environment and the lumen 208. In alternative embodiments, a side-port 600 is formed radially through a portion of the electrode 106.

Figure 2A:
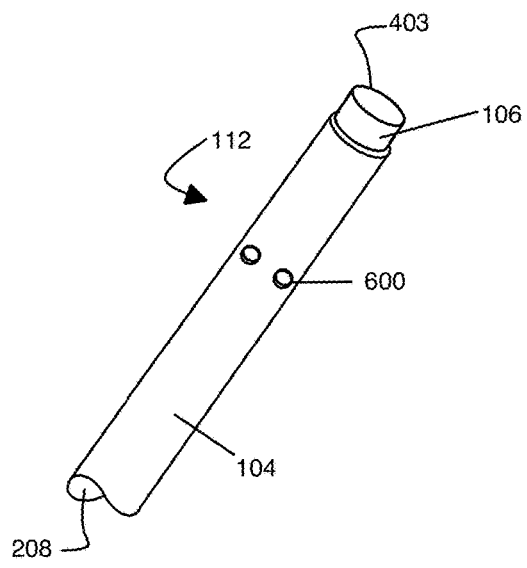
FIGS. 2A to 2D, in partial perspective views, illustrate distal regions of embodiments of medical devices.
Figure 2B:
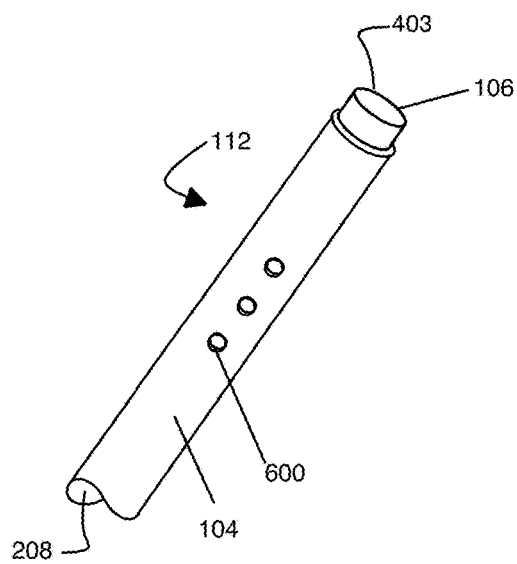
Figure 2C:
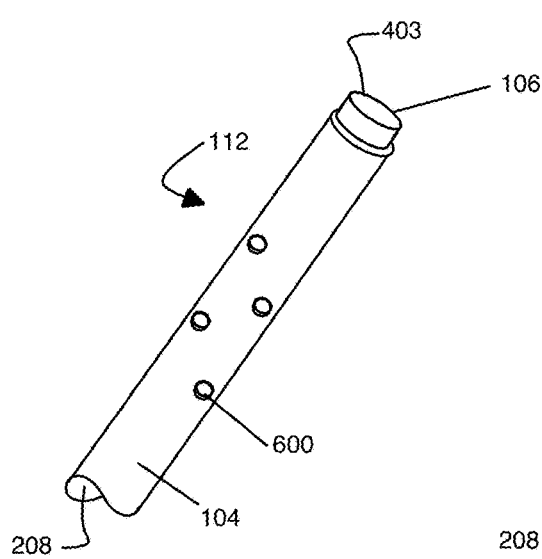
Figure 2D:
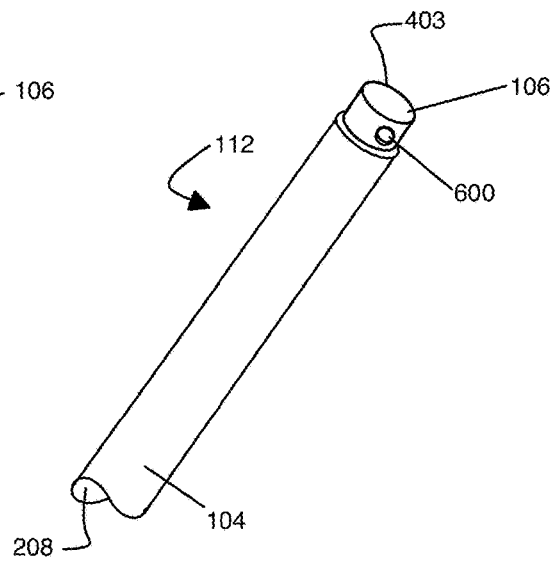

The size and shape of the side-port(s) 600 may vary depending on the intended application of the medical device 100, and the invention is not limited in this regard. For example, in one embodiment, the side-port(s) 600 is between about 0.25 mm and about 0.45 mm in diameter. Some embodiments include side-ports of more than one size. In addition, the number of side-ports 600 may vary, and they may be located anywhere along the medical device 100 that does not interfere with the functioning of the device. For example, as shown in FIG. 2A, the medical device 100 includes two side-ports 600 located about 1 cm from the distal end of the elongate member 102, at substantially the same longitudinal position along the elongate member 102. In another embodiment, as shown in FIG. 2B, the medical device 100 includes about 3 side-ports located at the same circumferential position and spaced longitudinally, for example at about 1.0, 1.5, and 2.0 cm from the distal end of the elongate member 102. In another embodiment, as shown in FIG. 2C, the side-port(s) 600 are staggered, such that they are spaced apart both circumferentially as well as longitudinally. In a further embodiment, as shown in FIG. 2D, the side-port(s) 600 are located on the electrode 106. In some embodiments, the side-port(s) 600 have a smooth or rounded wall, which serves to minimize or reduce trauma to bodily tissue. For example, some such embodiments comprise one or more side-port(s) 600 with a smooth outer circumferential edge created by sanding the circumferential edges to a smooth finish, or by coating the edges with a lubricious material, for example.

As previously described, when a medical device which relies on side-ports to provide fluid communication between its lumen and the surrounding environment is in a lumen of a close fitting member, the side-ports may be partially or completely occluded or blocked. The embodiments of FIGS. 4 to 9 relate to an apparatus which provide an effective conduit from the lumen of medical device to the environment outside of the device and methods of using such apparatus.

FIGS. 4A and 4B illustrate a partially cut away side view and an end view, respectively, of a distal part of distal section 112 of medical device 100 and of tubular member 800. As described in more detail hereinbelow, some embodiments of medical device 100 are comprised of a single piece elongate member 102 (e.g. FIGS. 1 and 10A) and some other embodiments of medical device 100 are comprised of two elongate members, main member 210 and end member 212, which are joined together (e.g. FIGS. 10D, 2E). Depending on the embodiment of medical device 100 being considered, distal section 112 may be the distal section of a single piece elongate member 102, the distal section of an end member 212, or the distal section of some other embodiment of medical device 100. In FIGS. 4 to 9, the lumen defined by distal section 112 may be either lumen 208 of elongate member 102 or end member lumen 216; for descriptive purposes, the lumen defined by distal section 112 in FIGS. 4 to 9 is referred to as device lumen 809.

Tubular member 800 may comprise either a dilator, or a sheath, or some other member defining a lumen configured to receive a medical device 100.

Referring to FIGS. 4A and 4B, distal section 112 of medical device 100 includes change in diameter 831, a distal portion 830, device lumen 809 defined by a body of the medical device 100, a side-port 600 in fluid communication with the lumen, and a closed distal end (i.e. the device does not have a distal face aperture). Distal portion 830 has an outer diameter less than the outer diameter of distal section 112 proximal of the change in diameter 831 i.e. distal portion 830 has a reduced diameter. In the embodiment of FIG. 4A, distal tip 403 of the medical device comprises a distal electrode 106. Some alternative embodiments of medical device 100 do not include an electrode. Tubular member 800 defines tubular member lumen 802. Tubular member 800 and distal portion 830 of medical device 100, in combination, define conduit 808 whereby medical device 100 is able to provide sufficient fluid flow for delivering contrast fluid to stain tissue. Fluid (e.g. blood) may also be withdrawn through the path defined by conduit 808, side-port 600, and device lumen 809. In the example of FIG. 4A, conduit 808 includes the space between tubular member 800 and reduced diameter distal portion 830, and the portion of tubular member lumen 802 which is distal of medical device 100.

In the embodiment of FIG. 4A, distal portion 830 is distal of change in diameter 831 and includes insulated part 834 and electrode 106. Constant diameter part 836 is distal of change in diameter 831 and includes insulated part 834 and the straight longitudinal part of electrode 106 which has a constant diameter (it does not include the dome shaped tip of electrode 106). Constant diameter part 836 of distal portion 830 does not taper and may be described as having a substantially constant diameter longitudinally. There is a minor change in outer diameter at the distal end of electrical insulator 104, but with regards to fluid flow, it can be considered negligible.

In the embodiment of FIG. 4A, a part of distal portion 830 is proximal of side-port 600 and there is a small space or gap 832 between the part of distal section 112 proximal of the change in diameter 831 and tubular member 800. It is common for embodiments of medical device 100 and tubular member 800, when in use, to have a small gap 832 between them because having the parts fitting closely enough to completely eliminate the gap would result in increased friction between the medical device and tubular member and could result in it being difficult to advance medical device 100 through tubular member 800. In typical embodiments, the gap is small enough that it prevents a substantial flow of fluids proximal of the side-port 600, such as for example, contrast fluids which are typically 3 to 5 times more viscous than water.

In the embodiment of FIG. 4A, side-port 600 is close to the change in diameter 831 whereby the larger diameter part of distal section 112 functions as a brace to keep tubular member 800 from blocking side-port 600. FIG. 4A illustrates an abrupt change in diameter. Alternative embodiments have a less abrupt change in diameter. Typical embodiments of medical device 100 include a second side-port, with the two side-ports being opposite to each other. Some alternative embodiments include more than two side-ports. Other alternative embodiments have one side-port. In some alternative embodiments of medical device 100, side-port 600 is longitudinally elongated i.e. capsule-shaped.

The side-port(s) 600 and the device lumen 809 together provide a pressure transmitting lumen. The pressure transmitting lumen is operable to be coupled to a pressure transducer, for example, external pressure transducer 708 (to be described with respect to FIG. 8), to thereby provide a pressure sensor.

While distal tip 403 of medical device 100 is shown in the example of FIG. 4A as being slightly proximal of the distal end of tubular member 800, fluid communication is still provided: if distal tip 403 is aligned with the distal end of tubular member 800; if distal tip 403 is positioned further proximal of the distal end of tubular member 800; or distal of the distal end of tubular member 800. If distal tip 403 is positioned such that side-port 600 is distal of the distal end of tubular member 800, it is still possible to deliver fluid in a radial direction.

Typical embodiments of medical device 100 comprise a conductive member (elongate member 102, or main member 210 joined to end member 212), which is typically comprised of a metallic material. The conductive member is in electrical communication with distal electrode 106 and a layer of insulation (electrical insulator 104) covers the metallic material. In other words, the elongate member 102 comprises an electrically conductive material, and a layer of insulation covers the electrically conductive material, the electrically conductive material being electrically coupled to the electrode 106. For some single piece embodiments, elongate member 102 has an on outer diameter proximal of change in diameter 831 of about 0.7 mm to about 0.8 mm at distal end 206 and an outer diameter for reduced diameter distal portion 830 of about 0.4 mm to about 0.62 mm. For some two piece embodiments, end member 212 has an outer diameter proximal of change in diameter 831 of about 0.40 mm to about 0.80 mm and an outer diameter for distal portion 830 of about 0.22 mm to about 0.62 mm. The above described embodiments are typically used with a tubular member defining a corresponding lumen about 0.01 mm (0.0005 inches) to about 0.04 mm (0.0015 inches) larger than the outer diameter of medical device 100 proximal of change in diameter 831.

FIG. 4B illustrates an end view of the apparatus of FIG. 4A. The figure includes, from inside to outside (in solid line): electrode 106, electrical insulator 104, the part of distal section 112 proximal of change in diameter 831, tubular member lumen 802, tubular member distal end 801 and tubular member 800. Hidden features shown in broken line include side-port 600 and device lumen 809.

In the embodiment of FIGS. 4A and 4B, distal tip 403 of the medical device is comprised of electrode 106 which defines a substantially circular cross-section and a circular end-profile. Similar to the embodiments of FIGS. 3A and 3B, electrode 106 of FIG. 4B is at the end of elongate member 102 (or end member 212) and has the same outer diameter as the distal end of the conductive member. Since constant diameter part 836 of reduced diameter distal portion 830 does not substantially taper (the small change in diameter at the distal end of electrical insulator 104 is not taken to be substantial), electrode 106 has a diameter which is substantially equal to the diameter of the part of distal portion 830 which is proximal of electrode 106 (i.e. substantially equal to the diameter of insulated part 834).

Making reference again to FIGS. 1 to 4, some embodiments of medical device 100 comprise an elongate member 102 having a closed distal end, with the elongate member defining a device lumen 809 and at least one side-port 600 in fluid communication with the device lumen. The elongate member also defines a proximal portion and a distal portion 830, the distal portion extending from the at least one side-port 600 to the distal end of the elongate member. The proximal portion defines a first outer diameter and the distal portion defines a second outer diameter, with the first outer diameter being larger than the second outer diameter and the second outer diameter being substantially constant. The distal tip of medical device 100 comprises an electrode 106. The diameter of the electrode is substantially equal to the second outer diameter.

Some embodiments of electrode 106 typically create a puncture in tissue with a diameter 10 to 20 percent larger than the electrode; such a puncture diameter is typically large enough to facilitate passage of the part of medical device proximal of change of diameter 831 (i.e. without the reduced diameter) through the tissue puncture and to start advancing a dilator over medical device 100 and through the tissue.

Figure 5D:
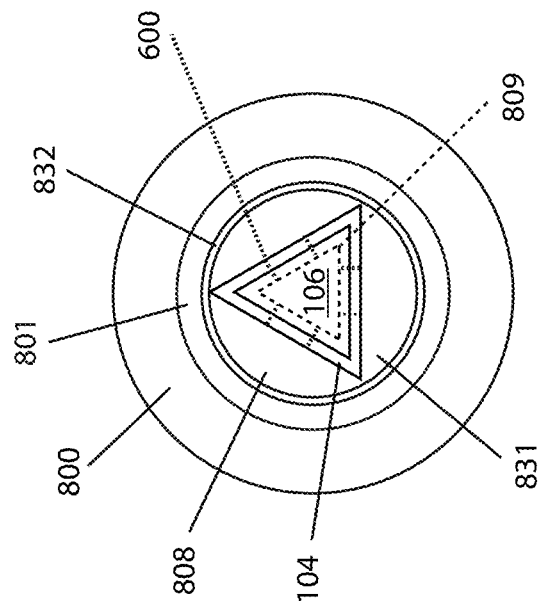
FIGS. 5C and 5D both illustrate end views of a medical device and a tubular member in accordance with alternative embodiments of the present invention.

FIGS. 5A to 5D illustrate embodiments of medical device 100 wherein distal portion 830 has a non-circular cross section. In FIGS. 5A and 5B, distal portion 830 (including insulated part 834 and electrode 106) defines a substantially flat outer surface portion. The body of medical device 100 defines device lumen 809 and side-port 600 in fluid communication with the lumen (shown in broken line in FIG. 5B). Reduced outer diameter distal portion 830 of the body extends between side-port 600 and distal tip 403 of the medical device whereby the outer surface of medical device 100, in combination with tubular member 800 can provide a conduit 808. While a portion of reduced outer diameter distal portion 830 extends proximally from side-port 600 to change in diameter 831, some alternative embodiments do not include this portion i.e. change in diameter 83 is adjacent side-port 600.

The embodiment of conduit 808 in FIG. 5B is shown as having an end-view shape of a portion of circle. The reduced outer diameter is substantially constant longitudinally along distal portion 830, with the exceptions of the distal end of electrical insulator 104 and the hemispherical-shaped distal tip of electrode 106. A cross-section of the electrode 106 is substantially identical to a cross-section of the part of the distal portion 830 which is proximal of the electrode.

Figure 5C:
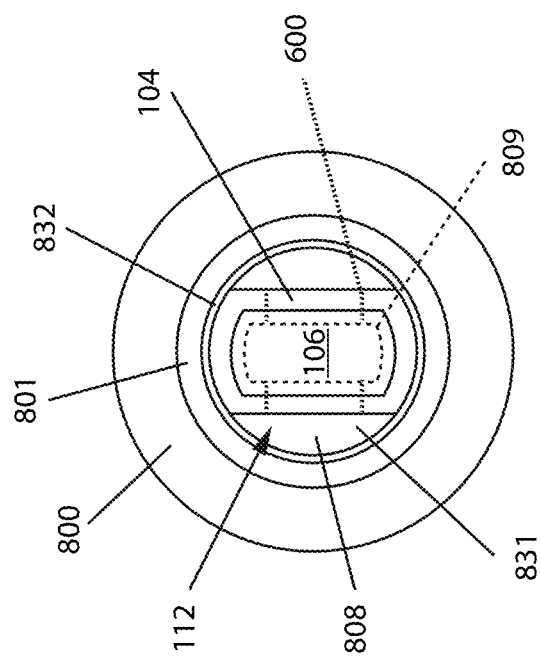

FIG. 5C illustrates an alternative embodiment with two flat outer surfaces and two corresponding side-ports and FIG. 5D illustrates another alternative embodiment with three flat outer surfaces and three corresponding side-ports. Further alternative embodiments are similar to the embodiments of FIGS. 5B, 5C and 5D, except instead of the flat outer surfaces, the devices have corresponding outer surfaces that are convexly curved to facilitate providing a larger device lumen 809.

Figure 6B:
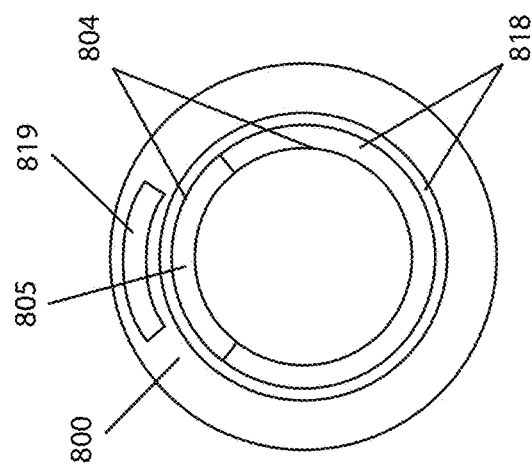
FIGS. 6A and 6B illustrate a partially cut away side view, and an end view, respectively, of a tubular member in accordance with another embodiment of the present invention.
Figure 6A:
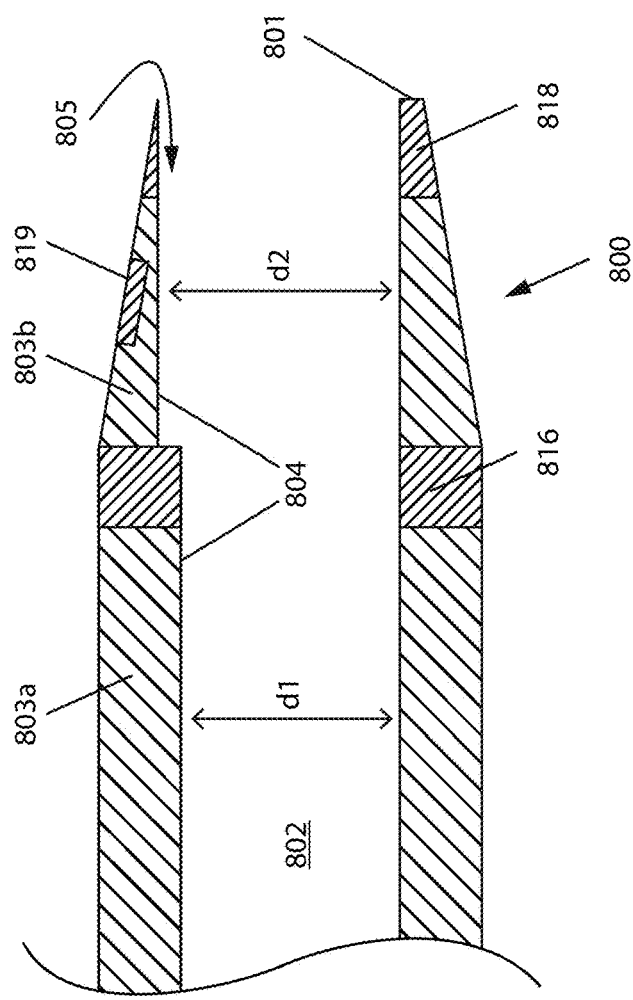

FIGS. 6A and 6B illustrate an embodiment of a tubular member 800 for use with a medical device 100 having a side-port 600. The body of tubular member 800 defines a lumen such that tubular member proximal region 803a has a first inner diameter d1, and tubular member distal region 803b has at least a portion of it defining a second inner diameter d2, wherein the second inner diameter d2 is greater than the first inner diameter d1 and wherein the tubular member distal region 803b extends to the tubular member distal end 801.

The embodiment of FIG. 6B includes the tubular member distal region 803b (the increased diameter portion with the second inner diameter d2) extending circumferentially over less than 360 degrees of the circumference of the tubular member. Tubular member inner surface 804 defines a tubular member channel 805, which in the example of FIG. 6B extends circumferentially approximately 90 degrees. In some alternative embodiments, tubular member distal region 803b extends 360 degrees of the circumference of the tubular body.

The embodiment of FIG. 6B includes tubular member proximal marker 816 at the proximal end of the distal region and tubular member distal marker 818 a proximal end marker at the distal end of tubular member distal region 803b. Alternative embodiments have only one of the distal region markers or neither distal region marker. The embodiment of FIGS. 6A and 6B also includes a side marker 819 which is operable to be used as an orientation marker for aligning the tubular member distal region 803b (the increased diameter portion) with the side-port 600 of a medical device 100 inserted through the tubular member.

One embodiment is a dilator comprising: a tubular member defining a lumen and a distal end aperture in fluid communication therewith; a proximal region having a first inner diameter; a distal region having an increased diameter portion defining a second inner diameter, the increased diameter portion extending proximally from a distal end of the dilator, the second inner diameter being substantially constant longitudinally; and he second inner diameter being greater than the first inner diameter.

The embodiment of FIGS. 7A and 7B is a kit comprising a tubular member 800 and a medical device 100, operable to be combined to form an apparatus. Tubular member 800 defines a tubular member lumen 802 for receiving medical device 100. Medical device 100 defines a device lumen 809 and a side-port 600 in fluid communication therewith, and comprises a medical device proximal region 838 proximal of the side-port and a medical device distal region 839 distal of the side-port. Medical device 100 and tubular member 800 are configured for cooperatively forming a conduit 808 between an outer surface of medical device distal region 839 and an inner surface of tubular member 800. In the example of FIG. 7A, conduit 808 is formed proximal and distal on side-port 600 while in alternative embodiments it is only formed distal of the side-port. In typical use, conduit 808 is formed at least between the side-port and a distal end of the tubular member when medical device 100 is inserted and positioned within tubular member lumen 802.

The apparatus of FIG. 7A includes both a tubular member channel 805 and a medical device channel 807. Conduit 808 is comprised of both tubular member channel 805 and a medical device channel 807. In typical embodiments, at least some of the length of conduit 808 has a constant cross-sectional configuration, which reduces turbulence and facilitates laminar flow, which in turn facilitates forwards injection of a fluid. Some alternative embodiments include a tubular member channel 805 but not a medical device channel 807 and some other alternative embodiments include a medical device channel 807 but not a tubular member channel 805.

Some embodiments of the medical device and the tubular member further comprise corresponding markers for aligning the side-port of the medical device within the tubular member lumen to form said conduit. In the example of FIG. 7, medical device 100 includes medical device proximal marker 810 and medical device distal marker 812, and tubular member 800 includes side marker 819. In some embodiments of the kit, the corresponding markers are configured for longitudinally aligning the side-port within the tubular member lumen. In the example of FIG. 7, side-port 600, which is equidistant between medical device proximal marker 810 and medical device distal marker 812, can be longitudinally aligned with side marker 819 by positioning side marker 819 between medical device proximal marker 810 and medical device distal marker 812.

In some embodiments of the kit, the corresponding markers are configured for rotationally aligning the side-port within the tubular member lumen. In the example of FIG. 7, side-port 600 can be rotationally aligned with side marker 819 of tubular member 800 by comparing the relatively larger diameter medical device proximal marker 810 with the smaller diameter medical device distal marker 812, which thereby aligns side-port 600 with tubular member channel 805. Alternative embodiments of medical device 100 include a side-marker on the same side as side-port 600 or on the side opposite to the side-port to facilitate rotational positioning. Further details regarding markers are found in U.S. Pat. No. 4,774,949, issued Oct. 4, 1988 to Fogarty, incorporated by reference herein in its entirety.

An embodiment of a kit comprises: a tubular member defining a tubular member lumen and a distal end aperture in fluid communication therewith; a a medical device having a closed distal end, the medical device defining a device lumen and at least one side-port in fluid communication therewith, the medical device defining a distal portion extending from the at least one side-port to a distal end of the medical device; and the medical device and tubular member being configured to cooperatively form a conduit between an outer surface of the distal portion and an inner surface of the tubular member when the medical device is inserted within the tubular member lumen, the conduit being formed at least between the side-port and the distal end aperture for enabling fluid communication between the side-port and an environment external to the distal end aperture.

In a specific embodiment of a kit, end member 212 has an on outer diameter proximal of change in diameter 831 of about 0.032 inches (about 0.81 mm) and an out diameter for reduced diameter distal portion 830 of about 0.020 inches (about 0.51 mm) to about 0.025 inches (about 0.64 mm) and is used with a tubular member defining a lumen about 0.0325 inches (0.82 mm) to about 0.0335 inches (0.85 mm).

Figure 8:
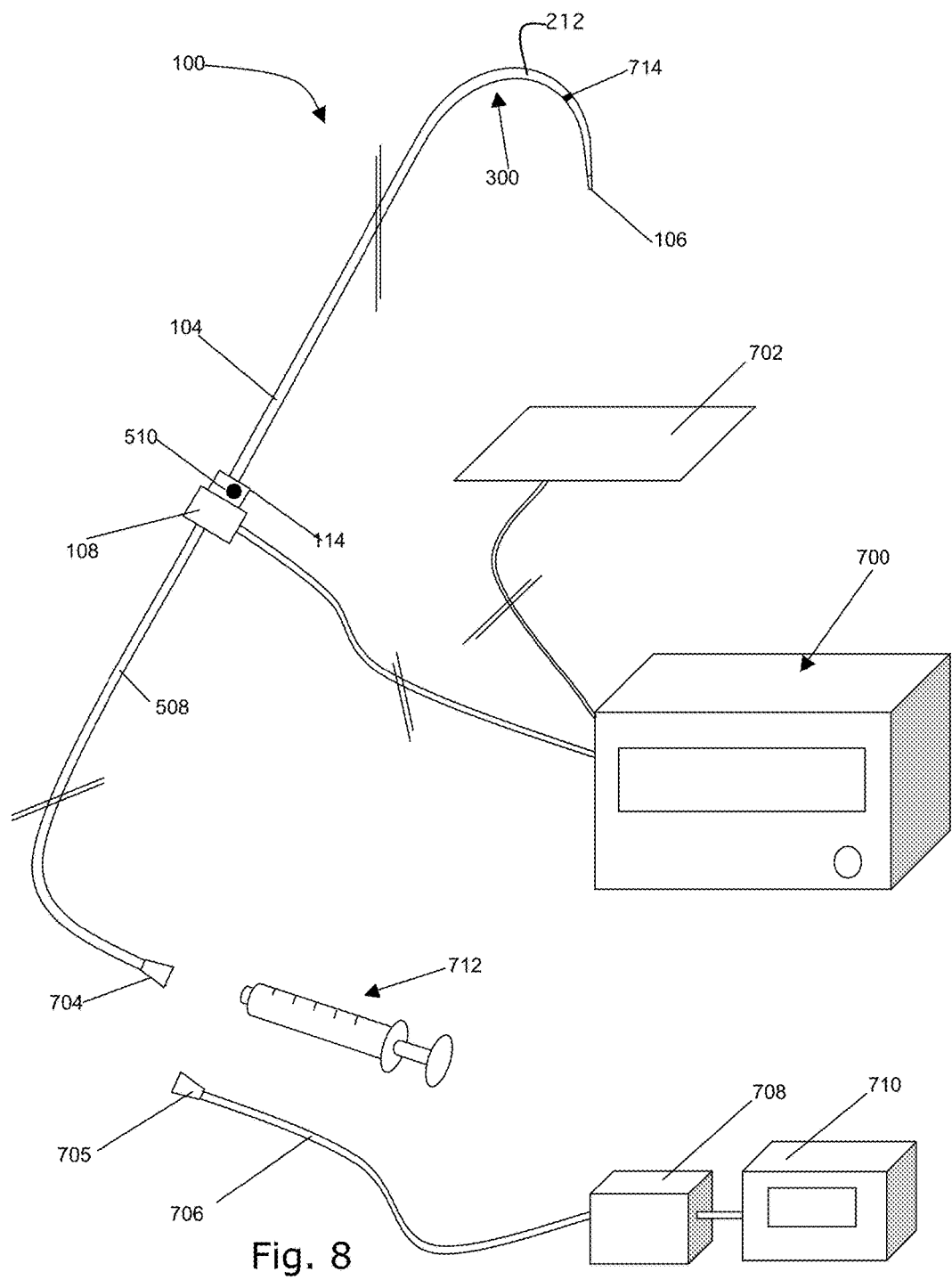
FIG. 8, in a perspective view, illustrate a system including a medical device in accordance with the present invention.

Referring to FIG. 8, systems for use with the medical device 100 typically comprise a generator 700 and, in some embodiments, a grounding pad 702, tubing, a pressure transducer, and/or a source of fluid 712.

Referring to FIG. 8, as mentioned hereinabove, in order to measure pressure at the distal region 202 of the medical device 100, an external pressure transducer may be coupled to the medical device 100. In the example of FIG. 8, an adapter 705 is operatively coupled to the external tubing 706, which is operatively coupled to an external pressure transducer 708. The adapter 705 is structured to facilitate coupling to adapter 704 when in use. In some examples, adapters 704 and 705 comprise male and female Luer locks or other connectors, adapted to readily couple and decouple to/from each other. In use, tubing 706 and 508 may be flushed with saline or another suitable fluid to remove air bubbles prior to measuring pressure. When medical device 100 is positioned in a vessel, conduit or cavity of a body, fluid adjacent the distal region 202 exerts pressure through the side-port(s) 600 on fluid within the lumen 208, which in turn exerts pressure on fluid in tubing 508 and 706, which further exerts pressure on external pressure transducer 708. The side-port(s) 600 and the lumen 208 thus provide a pressure sensor in the form of a pressure transmitting lumen for coupling to a pressure transducer.

The external pressure transducer 708 produces a signal that varies as a function of the pressure it senses. The external pressure transducer 708 is electrically coupled to a pressure monitoring system 710 that is operative to convert the signal provided by the transducer 708 and display a pressure contour as a function of time, for example. Thus, pressure is optionally measured and/or recorded and, in accordance with one embodiment of a method aspect as described further herein below, used to determine a position of the distal region 202. In those embodiments of the medical device 100 that do not comprise a lumen in fluid communication with the outside environment, a pressure transducer may be mounted at or proximate to the distal section 112 of the medical device 100 and coupled to a pressure monitoring system, for example via an electrical connection.

As previously mentioned, for some embodiments the medical device 100 is operatively coupled to a source of fluid 712 for delivering various fluids to the medical device 100 and thereby to a surrounding environment. The source of fluid 712 may be, for example, an IV bag or a syringe. The source of fluid 712 may be operatively coupled to the lumen 208 via the tubing 508 and the adapter 704, as mentioned hereinabove. Alternatively, or in addition, some embodiments include the medical device 100 being operatively coupled to an aspiration device for removing material from the patient's body through one or more of the side-ports 600.

In one broad aspect, the medical apparatus is used in a method of establishing a conduit for fluid communication for a medical device 100, the medical device defining a device lumen 809 and a side-port 600 in fluid communication with the device lumen. Making reference to FIGS. 4 to 9, the method comprises the steps of: (a) inserting a medical device 100 having at least one side-port 600 into a tubular member 800; and (b) cooperatively defining a conduit 808 for fluid communication by positioning the side-port 600 of the medical device 100 at a location of the tubular member 800 for which a space exists between the side-port 600 and an inner wall of the tubular member (tubular member inner surface 804), the space forming a part of the conduit 808 at least between the side-port 600 and a distal end of the tubular member.

In some embodiments of the broad aspect, the medical device comprises a medical device proximal marker 810 proximal of the side-port, and a medical device distal marker 812 distal of the side-port, and step (b) includes visualizing at least one of the proximal marker and the distal marker to position the medical device. In some such embodiments, step (b) comprises positioning side-port 600 within tubular member lumen 802, for example by using a medical device proximal marker 810 and a medical device distal marker 812. In such embodiments of the method, it not necessary for distal tip 403 to be inside of tubular member lumen 802. In some embodiments of the method, the medical device further comprises a side-port marker wherein the side-port marker and the side-port are equi-distant from a tip of the medical device, and wherein step (b) includes visualizing the side-port marker to position the medical device. In some other embodiments, step (b) comprises positioning distal portion 830 of distal section 112 within tubular member lumen 802, which inherently positions the side-port in the tubular member lumen. In some embodiments of the method, step (b) includes aligning a distal tip 403 of the medical device with the tubular member distal end 801.

Some embodiments of the broad aspect further comprise a step (c) of delivering fluid through the side-port 600 wherein the fluid is a contrast fluid 814 and wherein step (c) includes delivering the contrast fluid distally through the distal end of the tubular member. Some such embodiments further comprise, before the contrast fluid is delivered, a step of delivering electrical energy to puncture tissue. Some embodiments comprise, after the contrast fluid is delivered, a step (d) of delivering electrical energy through the medical device to create a puncture through a tissue.

In some embodiments, the tissue comprises a septum of a heart, and step (c) comprises staining the septum by delivering contrast fluid through the side-port.

In some embodiments of the broad aspect, the side-port 600 and the device lumen 809 together comprise a pressure transmitting lumen, and the method further comprises a step (c) of measuring a pressure of an environment external to the distal end using the side-port and the conduit. Some such embodiments further comprise a step (d) of delivering fluid through the side-port.

Some embodiments of the broad aspect further comprise a step (c) of withdrawing fluid through the side-port 600. In some such embodiments, the fluid is blood.

Figure 9A:
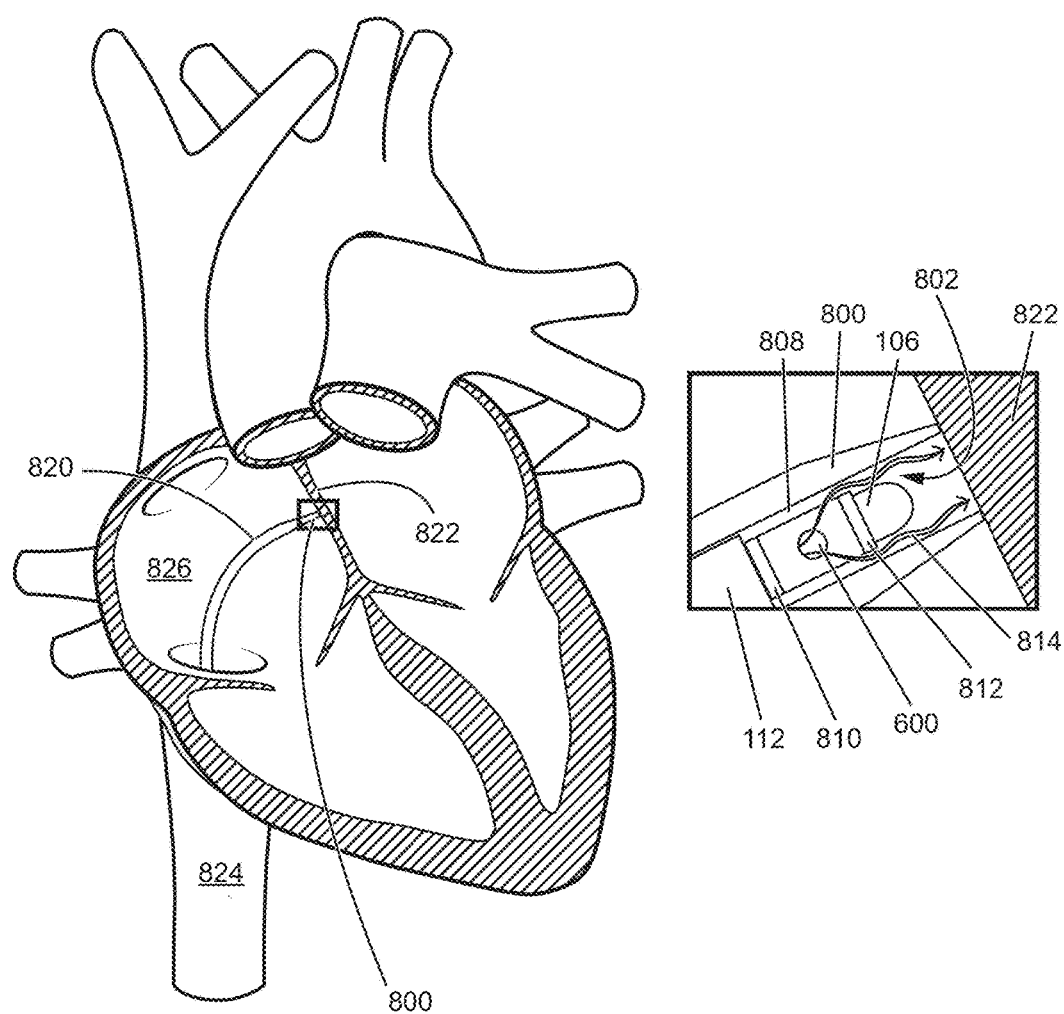
FIGS. 9A and 9B illustrate partially cut away views of a method using an apparatus in accordance with an embodiment of the present invention.
Figure 9B:
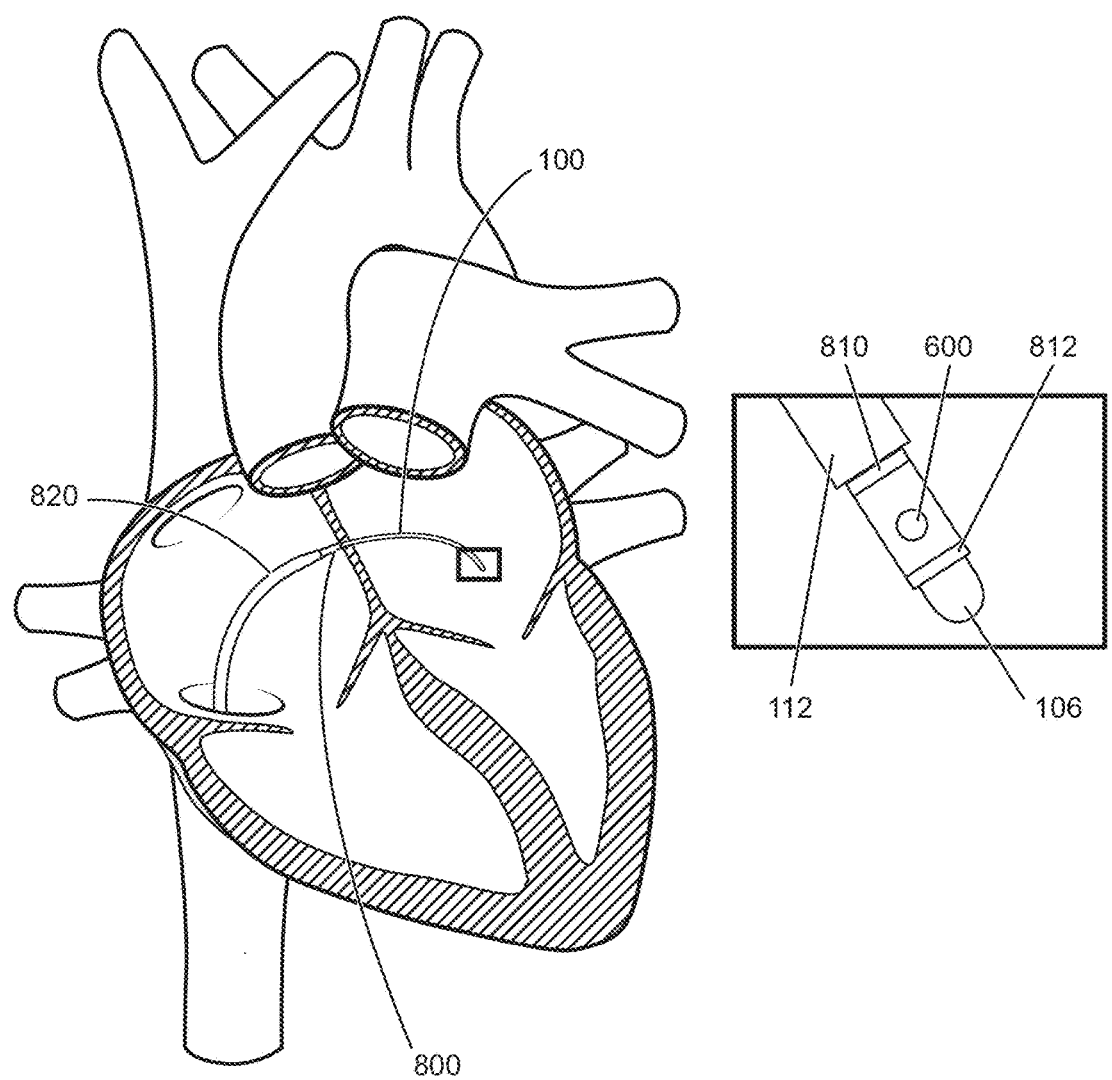

In one example of a method of use, illustrated in FIGS. 9A and 9B, a target site comprises a tissue within the heart of a patient, the atrial septum 822. In this example, the target site is accessed via the inferior vena cava (IVC), for example through the femoral vein. The medical device 100 of FIGS. 9A and 9B is similar to medical device of FIG. 4A, except the embodiment of FIG. 9 has a medical device proximal marker 810 and a medical device distal marker 812.

The example of the method includes a user advancing sheath 820 and a dilator (tubular member 800) through inferior vena cava 824 and introducing the sheath and tubular member 800 into the right atrium 826 of the heart. An electrosurgical device, for example medical device 100 described hereinabove, is then introduced into tubular member lumen 802, and advanced toward the heart. In typical embodiments of the method, these steps are performed with the aid of fluoroscopic imaging.

After inserting medical device 100 into tubular member 800, the user positions the distal end of tubular member 800 against the atrial septum 822 (FIG. 9A). Some embodiments of tubular member 800 include markers (FIG. 6A). The medical device is then positioned such that electrode 106 is aligned with or slightly proximal of the distal end of tubular member 800 (FIG. 9A insert). Medical device proximal marker 810 and medical device distal marker 812 facilitate positioning medical device 100. Tubular member 800 is typically positioned against the fossa ovalis of the atrial septum 822. Referring to the FIG. 9A insert, the inner surface of tubular member 800 and the outer surface of medical device 100 define conduit 808 from side-port 600 to the distal end of tubular member lumen 802, which is sealed by atrial septum 822.

Once medical device 100 and tubular member 800 have been positioned, additional steps can be performed, including taking a pressure measurement and/or delivering material to the target site, for example, a contrast agent, through side-port(s) 600. The FIG. 9A insert illustrates contrast fluid 814 flowing from side-port 600, through conduit 808, and ending at atrial septum 822, whereby the tissue is stained. In alternative examples, electrode 106 is positioned against atrial septum 822 when contrast fluid 814 is delivered. Such steps facilitate the localization of the electrode 106 at the desired target site.

Starting from the position illustrated by the FIG. 9A insert, medical device 100 is advanced until electrode 106 contacts atrial septum 822. Alternative embodiments having electrode 106 positioned against atrial septum 822 when contrast fluid 814 is delivered do not require this repositioning. With the medical device 100 and the dilator (tubular member 800) positioned at the target site, energy is delivered from an energy source, through medical device 100, to the target site. The path of energy delivery is through elongate member 102 (or main member 210 and end member 212), to the electrode 106, and into the tissue at the target site. The example of FIG. 9A includes delivering the energy being to vaporize cells in the vicinity of the electrode, thereby creating a void or puncture through the tissue at the target site and advancing distal section 112 of the medical device 100 at least partially through the puncture. When the distal section 112 has passed through the target tissue and reached the left atrium (FIG. 9B), energy delivery is stopped. The side-ports of medical device 100 are uncovered (FIG. 9B insert), whereby contrast is able to be delivered to confirm the position of distal section 112 in the left atrium of the heart. The diameter of the puncture created by the delivery of energy is typically large enough to facilitate advancing distal section 112 of the medical device 100 therethrough and to start advancing a dilator (tubular member 820).

Figure 10A:
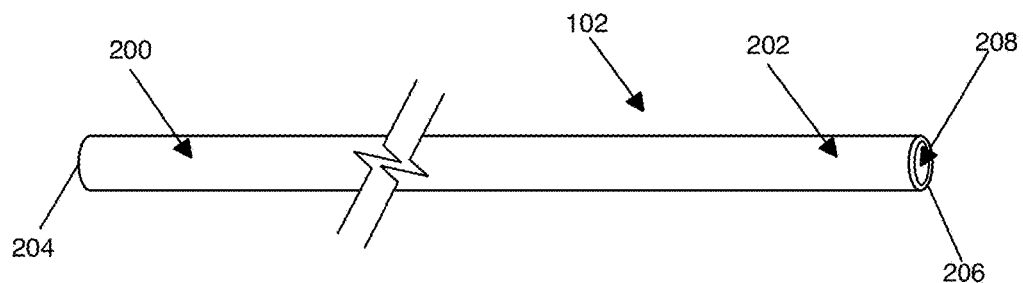
FIG. 10A, in a perspective view, illustrates an elongate member portion of the medical device shown in FIG. 1.

Referring now to FIG. 10A, the elongate member 102 includes a proximal region 200, a distal region 202, a proximal end 204, and a distal end 206. In some embodiments of the invention, the elongate member 102 defines a lumen 208, which typically extends substantially between the proximal region 200 and the distal region 202.

The elongate member 102 is typically sized such that the handle 110 remains outside of the patient when the distal end 206 is within the body, for example adjacent the target site. For example, the proximal end 204 is at a location outside of the body, while the distal end 206 is located within the heart of the patient. Thus, in some embodiments of the invention, the length of the elongate member 102, i.e. the sum of the force transmitting and distal section lengths, is between about 30 cm and about 100 cm, depending, for example, on the specific application and/or target site.

The transverse cross-sectional shape of the elongate member 102 may take any suitable configuration, and the invention is not limited in the regard. For example, the transverse cross-sectional shape of the elongate member 102 is substantially circular, ovoid, oblong, or polygonal, among other possibilities. Furthermore, in some embodiments, the cross-sectional shape varies along the length of the elongate member 102. For example, in one embodiment, the cross-sectional shape of the proximal region 200 is substantially circular, while the cross-sectional shape of the distal region 202 is substantially ovoid.

Figures 10B, 10C, 10D:
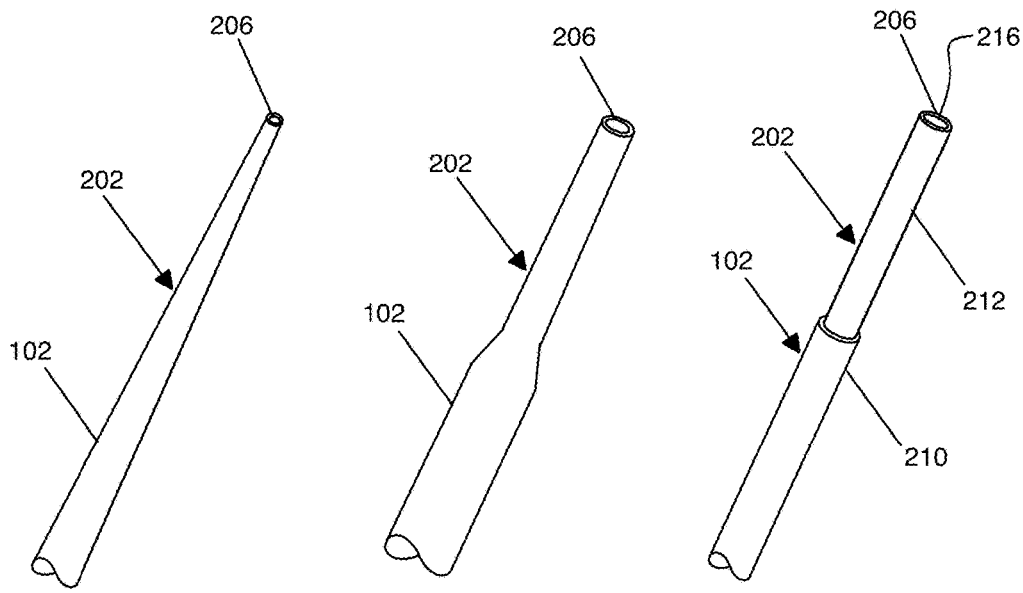
FIG. 10B, in a partial perspective view, illustrates an alternative elongate member usable in the medical device shown in FIG. 1.
FIG. 10C, in a partial perspective view, illustrates another alternative elongate member usable in the medical device shown in FIG. 1.
FIG. 10D, in a partial perspective view, illustrates yet another alternative elongate member usable in the medical device shown in FIG. 1.

In typical embodiments the outer diameter of the elongate member 102 is sized such that it fits within vessels of the body of the patient. For example, in some embodiments, the outer diameter of the elongate member 102 is between about 0.40 mm and about 1.5 mm (i.e. between about 27 Gauge and about 17 Gauge). In some embodiments, the outer diameter of the elongate member 102 varies along the length of the elongate member 102. For example, in some embodiments, the outer diameter of the elongate member 102 tapers from the proximal end 204 towards the distal end 206. In one specific embodiment, the outer diameter of the proximal region 200 of the elongate member 102 is about 1.5 mm. In this embodiment, at a point about 4 cm from the distal end 206, the outer diameter begins to decrease such that the distal end 206 of the elongate member 102 is about 0.7 mm in outer diameter. In a further embodiment, the outer diameter of the elongate member 102 tapers from about 1.3 mm to about 0.8 mm at a distance of about 1.5 mm from the distal end 206. FIG. 10B is an example of a taper in elongate member 102 occurring smoothly, for example over a length of about 4 cm, while FIG. 10C is an example of a taper occurring more abruptly, for example over a length of about 1 mm or less. The taper may be applied to the elongate member 102 by a variety of methods. In some embodiments, the elongate member 102 is manufactured with the taper already incorporated therein. In other embodiments, the elongate member 102 is manufactured without a taper, and the taper is created by swaging the elongate member down to the required outside diameter, or by machining the distal region 202 such that the outside diameter tapers while the inside diameter remains constant.

Figure 2E:
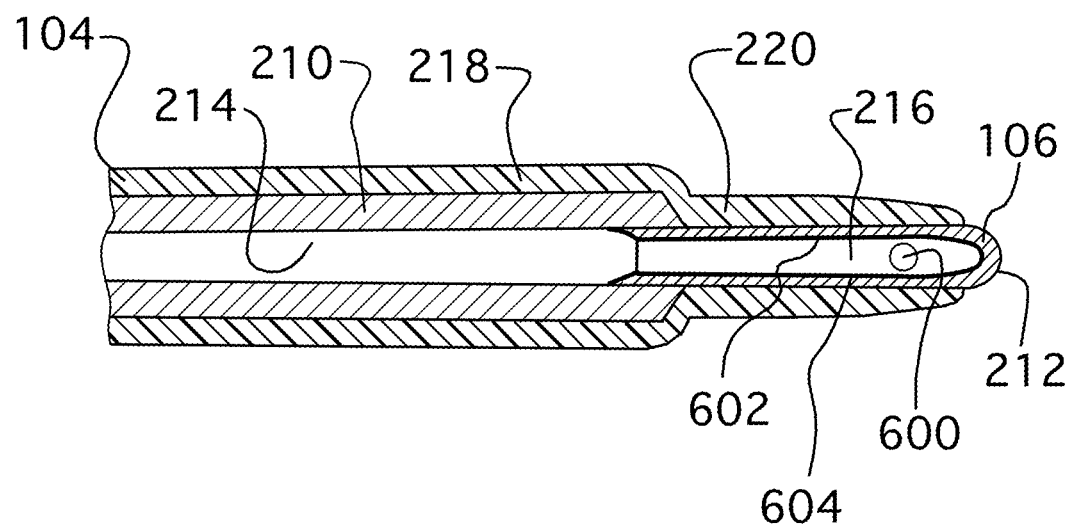
FIG. 2E, in cross-sectional view, illustrates a distal region of an embodiment of a medical device.

In a further embodiment, the elongate member 102 is manufactured from two pieces of material, each having a different diameter, which are joined together. For example, as shown in FIG. 10D, the elongate member 102 includes a main member 210 mechanically coupled to the handle (not shown in FIG. 10D), the main member 210 having for example a length of about 50 cm to about 100 cm and an outer diameter of about 1.15 mm to about 1.35 mm. The main member 210 defines a main member lumen 214, as shown in FIG. 2E, extending substantially longitudinally therethrough. An end member 212, having for example a length of about 2.5 cm to about 10 cm and an outer diameter of about 0.40 mm to about 0.80 mm, is joined to the main member 210, such that the main member 210 and end member 212 are co-axial. In some examples, the end member 212 is inserted partially into the main member lumen 214, substantially longitudinally opposed to the handle 110. In some embodiments, the electrode 106 is located about the end member, for example by being mechanically coupled to the end member 212, while in other embodiments the electrode 106 is integral with the end member 212. If the end member 212 defines an end member lumen 216, as seen in FIGS. 10D and 2E, the end member lumen 216 is in fluid communication with the main member lumen 214, as shown in FIG. 2E. The main member 210 and the end member 212 are joined in any suitable manner, for example welding, soldering, friction fitting, or the use of adhesives, among other possibilities. Also, in some embodiments, the main member lumen 214 and the end member lumen 216 have substantially similar diameters, which reduce turbulence in fluids flowing through the main member lumen 214 and the end member lumen 216.

In embodiments of the invention wherein the elongate member 102 defines a lumen 208, the wall thickness of the elongate member 102 may vary depending on the application, and the invention is not limited in this regard. For example, if a stiffer device is desirable, the wall thickness is typically greater than if more flexibility is desired. In some embodiments, the wall thickness in the force transmitting region is from about 0.05 mm to about 0.40 mm, and remains constant along the length of the elongate member 102. In other embodiments wherein the elongate member 102 is tapered, the wall thickness of the elongate member 102 varies along the elongate member 102. For example, in some embodiments, the wall thickness in the proximal region 200 is from about 0.1 mm to about 0.4 mm, tapering to a thickness of from about 0.05 mm to about 0.20 mm in the distal region 202. In some embodiments, the wall tapers from inside to outside, thereby maintaining a consistent outer diameter and having a changing inner diameter. Alternative embodiments include the wall tapering from outside to inside, thereby maintaining a consistent inner diameter and having a changing outer diameter. Further alternative embodiments include the wall of the elongate member 102 tapering from both the inside and the outside, for example by having both diameters decrease such that the wall thickness remains constant. For example, in some embodiments, the lumen 208 has a diameter of from about 0.4 mm to about 0.8 mm at the proximal region 200 and tapers to a diameter of from about 0.3 mm to about 0.5 mm at the distal region 202. In other alternative embodiments, the outer diameter decreases while the inner diameter increases, such that the wall tapers from both the inside and the outside.

In some embodiments, the elongate member 102, and therefore the medical device 100, are curved or bent, as shown in FIGS. 11A-11C. As used herein, the terms 'curved' or 'bent' refer to any region of non-linearity, or any deviation from a longitudinal axis of the device, regardless of the angle or length of the curve or bend. The medical device 100 includes a substantially rectilinear section 302 and a curved section 300 extending from the substantially rectilinear section 302. Typically, the curved section 300 is located in the distal region 202 of the elongate member 102, and may occur over various lengths and at various angles. In some examples, curved section 300 has a relatively large radius, for example between about 10 cm and about 25 cm, and traverses a small portion of a circumference of a circle, for example between about 20 and about 40 degrees, as shown in FIG. 11B. In alternative examples, the curved section 300 has a relatively small radius, for example between about 4 cm and about 7 cm, and traverses a substantially large portion of a circumference of a circle, for example between about 50 and about 110 degrees, as shown in FIG. 11C. In one specific embodiment, the curved section 300 begins about 8.5 cm from the distal end 206 of the elongate member 102, has a radius of about 6 cm, and traverses about 80° of a circumference of a circle. In an alternative embodiment, the curved section has a radius of about 5.4 cm and traverses about 50° of a circumference of a circle and, in a further embodiment, the curved section has a radius of about 5.7 cm and traverses about 86° of a circumference of a circle. This configuration helps in positioning the elongate member 102 such that the 206 is substantially perpendicular to the tissue through which the channel is to be created, which transmits the most energy through the elongate member 102 upon a force being exerted thereonto, giving enhanced feedback to the intended user.

The curved section 300 may be applied to the elongate member 102 by a variety of methods. For example, in one embodiment, the elongate member 102 is manufactured in a curved mold. In another embodiment, the elongate member 102 is manufactured in a substantially straight shape, and placed in a heated mold to force the elongate member 102 to adopt a curved shape. Alternatively, the elongate member 102 is manufactured in a substantially straight shape and is forcibly bent by gripping the elongate member 102 just proximal to the region to be curved and applying force to curve the distal region 202. In an alternative embodiment, the elongate member 102 includes a main member 210 and an end member 212, as described with respect to FIG. 10D, which are joined together at an angle (not shown in the drawings). That is, rather than being coaxial, the main member 210 and an end member 212 are joined such that, for example, they are at an angle of 45° with respect to each other.

As mentioned hereinabove, in some embodiments the proximal region 200 of the elongate member 102 is structured to be coupled to a source of energy. An example is the proximal region 200 comprising a hub 108, to which an energy source is connected, and which allows for the energy source to be electrically connected to the elongate member 102. Further details regarding the hub 108 are described hereinbelow. In other embodiments, the proximal region 200 is coupled to a source of energy by other methods known to those of skill in the art, and the invention is not limited in this regard.

In typical embodiments, the elongate member 102 is made from an electrically conductive material that is biocompatible. As used herein, 'biocompatible' refers to a material that is suitable for use within the body during the course of a surgical procedure. Such materials include stainless steels, copper, titanium and nickel-titanium alloys (for example, NITINOL®), amongst others. Furthermore, in some embodiments, different regions of the elongate member 102 are made from different materials. In an example of the embodiment of FIG. 10D, the main member 210 is made from stainless steel, such that it provides column strength to a portion of the elongate member 102, for example to the force transmitting section, and the end member 212 is made out of a nickel-titanium alloy, such as NITINOL®, such that it provides flexibility to a portion of the elongate member 102, for example the distal section. Embodiments wherein the force transmitting section of the elongate member 102 is manufactured from stainless steel, for example, often result in medical device 100 having a similar amount of column strength to a device of the prior art, for example a mechanical perforator such as a Brockenbrough™ needle. This is beneficial in that it provides a familiar 'feel' to users who have used such devices in the past. In some embodiments comprising a curved or bent elongate member 102, the rectilinear section 302 is made from stainless steel, such that it provides column strength to the elongate member 102, and the curved section 300 is made out of a nickel-titanium alloy, such as NITINOL®, such that it provides flexibility to the elongate member 102. In addition, the use of NITINOL® for curved section 300 is advantageous as the superelastic properties of this material helps in restoring the shape of the curved section 300 after the curved section 300 is straightened out, for example when placed within a dilator.

As mentioned hereinabove, the elongate member 102 has an electrical insulator 104 disposed on at least a portion of the outer surface thereof. In some embodiments, for example as shown in FIG. 1, electrical insulator 104 covers the circumference of the elongate member 102 from the proximal region 200 of the elongate member 102 to the distal region 202 of the elongate member 102. In other words, the force transmitting section 114 and distal section 112 are electrically conductive and the electrical insulator substantially covers the force transmitting section 114 and distal section 112 with the electrode 106 substantially deprived from the electrical insulator 104. When a source of energy is coupled to the proximal region 200 of the elongate member 102, the electrical insulator 104 substantially prevents leakage of energy along the length of the elongate member 102, thus allowing energy to be delivered from the proximal region 200 of the elongate member 102 to the electrode 106.

In embodiments such as illustrated in FIG. 1, the location in the distal region 202 to which electrical insulator 104 extends depends on the configuration of the electrode 106. Typically, electrical insulator 104 extends to a proximal end 404 of the electrode 106, which may or may not coincide with the distal end of the elongate member 102. For example, as shown in FIG. 3A, the distalmost 1.5 mm of the elongate member 102 serves as at least a portion of the electrode 106. In these embodiments, electrical insulator 104 extends to a point about 1.5 mm proximal to the distal end 206 of the elongate member 102. In the embodiments of FIGS. 3B-3C, an external component 400 coupled to the distal end of the elongate member 102 serves as the electrode 106. In such embodiments, the proximal end 404 of the electrode 106 substantially coincides with the distal end 206 of the elongate member 102, and thus the electrical insulator 104 extends to the distal end 206 of the elongate member 102. In some embodiments, the electrical insulator 104 extends beyond the distal end 206 of the elongate member 102, and covers a portion of the external component 400. This typically aids in securing the external component 400 to the elongate member 102. The uncovered portion of the external component 400 can then serve as the electrode 106. In other embodiments, for example as shown in FIG. 3A, the distalmost portion of the elongate member 102, as well as an external component 400, serve as the electrode 106. In this embodiment, the electrical insulator 104 extends to a point substantially adjacent to the distal end 206 of the elongate member 102. In one example, the electrical insulator 104 extends to a point about 1.0 mm away from the distal end 206 of the elongate member 102.

The electrical insulator 104 may be one of many biocompatible dielectric materials, including, but not limited to, polytetrafluoroethylene (PTFE, Teflon®), parylene, polyimides, polyethylene terepthalate (PET), polyether block amide (PEBAX®), and polyetheretherketone (PEEK™), as well as combinations thereof. The thickness of the electrical insulator 104 may vary depending on the material used. Typically, the thickness of the electrical insulator 104 is from about 0.02 mm to about 0.12 mm.

In some embodiments, the electrical insulator 104 comprises a plurality of dielectric materials. This is useful, for example, in cases where different properties are required for different portions of the electrical insulator 104. In certain applications, for example, substantial heat is generated at the electrode 106. In such applications, a material with a sufficiently high melting point is required for the distalmost portion of the electrical insulator 104, so that this portion of the electrical insulator 104, located adjacent to electrode 106, doesn't melt. Furthermore, in some embodiments, a material with a high dielectric strength is desired for all or a portion of the electrical insulator 104. In some particular embodiments, electrical insulator 104 has a combination of both of the aforementioned features.

With reference now to FIG. 2E, the electrical insulator 104 includes a first electrically insulating layer 218 made out of a first electrically insulating material, the first electrically insulating layer 218 substantially covering the main member 210 substantially adjacent the end member 212 and a second electrically insulating layer 220 made out of a second electrically insulating material, the second electrically insulating layer 220 substantially covering the end member 212 with the electrode 106 substantially deprived from the second electrically insulating layer 220, said second electrically insulating layer 220 being substantially thinner than the first electrically insulating layer 218. In the illustrated embodiment, the first electrically insulating layer 218 overlaps the second electrically insulating layer 220 about the region of the taper of the elongate member 102. This configuration facilitates the obtention of desirable mechanical properties for the medical device 100, as thinner materials are typically less rigid than thicker materials. Also, in some embodiments of the invention, the first electrically insulating layer 218 overlaps a portion of the second electrically insulating layer 220. However, in alternative embodiments of the invention, the electrical insulator 103 has any other suitable configuration, for example, the first electrically insulating layer 218 and the second electrically insulating layer 220 being made of the same material.

Figure 3D:
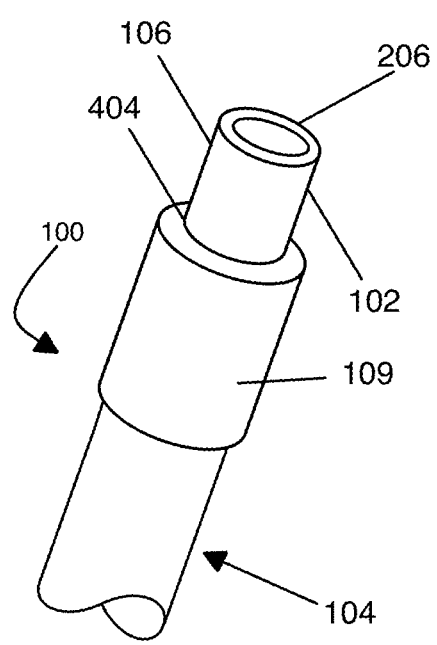

In further embodiments, for example in order to prevent a distal section of the electrical insulator 104 from melting due to heat generated by the electrode 106, a heat shield 109 is applied to the medical device 100 substantially adjacent to the electrode 106, as shown in FIG. 3D. For example, in some such embodiments, a thermally insulating material, for example Zirconium Oxide or polytetrafluoroethylene (PTFE), is applied over approximately the distal-most 2 cm of the electrical insulator 104. Typically, the heat shield 109 protrudes substantially radially outwardly from the remainder of the distal section 112 and substantially longitudinally from the electrode 106 in a direction leading towards the handle 110.

The electrical insulator 104 may be applied to the elongate member 102 by a variety of methods. For example, if the electrical insulator 104 includes PTFE, it may be provided in the form of heat-shrink tubing, which is placed over the elongate member 102 and subjected to heat to substantially tighten around the elongate member 102. If the electrically insulative material is parylene, for example, it may be applied to the elongate member 102 by vapor deposition. In other embodiments, depending on the specific material used, the electrical insulator 104 may be applied to the elongate member 102 by dip-coating, co-extrusion, or spraying, for example.

As mentioned hereinabove, in embodiments of the present invention, the elongate member 102 comprises an electrode 106 at the distal region thereof, the electrode 106 configured to create a channel via radiofrequency perforation. As used herein, 'radiofrequency perforation' refers to a procedure in which radiofrequency (RF) electrical energy is applied from a device to a tissue to create a perforation or fenestration through the tissue. Without being limited to a particular theory of operation, it is believed that the RF energy serves to rapidly increase tissue temperature to the extent that water in the intracellular fluid becomes converted to steam, inducing cell lysis as a result of elevated pressure within the cell. Furthermore, electrical breakdown may occur within the cell, wherein the electric field induced by the alternating current exceeds the threshold dielectric strength of the medium located between the radiofrequency perforator and the cell, causing a dielectric breakdown. In addition, mechanical breakdown may occur, wherein alternating current induces stresses on polar molecules in the cell. Upon the occurrence of cell lysis and rupture, a void is created, allowing the device to advance into the tissue with little resistance. In order to achieve this effect, the device from which energy is applied, i.e. the electrode, is relatively small, having an electrically exposed surface area of no greater than about 15 mm$^2$, in order to increase the current density delivered to the tissue. In addition, the energy source is capable of applying a high voltage through a high impedance load, as will be discussed further hereinbelow. This is in contrast to RF ablation, whereby a larger-tipped device is utilized to deliver RF energy to a larger region in order to slowly desiccate the tissue. As opposed to RF perforation, which creates a void in the tissue through which the device is advanced, the objective of RF ablation is to create a large, non-penetrating lesion in the tissue, in order to disrupt electrical conduction. Thus, for the purposes of the present invention, the electrode refers to a device which is electrically conductive and exposed, having an exposed surface area of no greater than about 15 mm$^2$, and which is, when coupled to a suitable energy source and positioned at a target site, operable to delivery energy to create a perforation or fenestration through tissue, for example by vaporizing intracellular fluid of cells with which it is in contact, such that a void, hole, or channel is created in the tissue located at the target site.

In further embodiments, as shown in FIG. 3A, it is desirable for the distal end 206 of the elongate member 102 to be closed. For example, in some embodiments, it is desirable for fluids to be injected radially from the elongate member 102, for example through side-ports in elongate member 102 as discussed hereinbelow, substantially without being injected distally from the elongate member 102. In these embodiments, a closed distal end 206 facilitates radial injection of fluid while preventing distal injection.

Indeed, it is a common belief that it is necessary to have a distal opening in order to properly deliver a contrast agent to a target site. However, it was unpredictably found that it is nevertheless possible to properly operate the medical device 100 in the absence of distal openings. Advantageously, these embodiments reduce the risk that a core of tissue becomes first stuck in such a distal opening when creating the channel through the tissue and is afterwards freed into the blood circulation, which creates risks of blocking blood vessels, leading to potentially lethal infarctions.

Thus, as shown in FIG. 3A, an external component 400, for example an electrode tip, is operatively coupled to the distal end 206. In this embodiment, the exposed portion of the distal region 202, as well as the external component 400, serves as the electrode 106. In such an embodiment, if the outer diameter of the elongate member 102 is 0.7 mm, the external component 400 is a hemisphere having a radius of about 0.35 mm, and the length of the distalmost exposed portion of the elongate member 102 is about 2.0 mm, and then the surface area of the electrode 106 is about 5.2 mm$^2$. Alternatively, as shown for example in FIG. 2E, the distal end of end member 212, rather than a separate external component, is closed and is used as the electrode 106.

In other embodiments, as shown for example in FIGS. 3B and 3C, an electrically conductive and exposed external component 400 is electrically coupled to the distal end of the elongate member 102, such that the external component 400 serves as the electrode 106. In such an embodiment, external component 400 is a cylinder having a diameter of between about 0.4 mm and about 1 mm, and a length of about 2 mm. Electrode 106 thus has an exposed surface area of between about 2.6 mm$^2$ and about 7.1 mm$^2$.

The external component 400 may take a variety of shapes. Some examples, external component 400 are cylindrical, main, conical, or truncated conical. The distal end of the external component 400 may be rounded, or flat, for example. Furthermore, some embodiments of the external component 400 are made from biocompatible electrically conductive materials, for example stainless steel. The external component 400 may be coupled to the elongate member 102 by a variety of methods. In one embodiment, external component 400 is welded to the elongate member 102. In another embodiment, external component 400 is soldered to the elongate member 102. In one such embodiment, the solder material itself comprises the external component 400 e.g. an amount of solder being electrically coupled to the elongate member 102 in order to function as at least a portion of the electrode 106. In further embodiments, other methods of coupling external component 400 to the elongate member 102 are used, and the invention is not limited in this regard.

In these embodiments, as described hereinabove, the electrically exposed and conductive surface area of the electrode 106 is no greater than about 15 mm$^2$. In embodiments wherein the electrical insulator 104 covers a portion of the external component 400, the portion of the external component 400 that is covered by the electrical insulator 104 is not included when determining the surface area of the electrode 106.

Referring again to FIG. 3A, in some embodiments, the distal section 112 defines a distal tip 403, the distal tip 403 being substantially atraumatic. In other words, the distal end of the medical device 100 is structured such that it is substantially atraumatic, or blunt. As used herein the terms 'atraumatic' and 'blunt' refer to a structure that is not sharp, and includes structures that are rounded, obtuse, or flat, amongst others, as shown, for example, in FIG. 3A. In embodiments, wherein the distal end of the medical device 100 is substantially blunt, it is beneficial that unwanted damage to non-target areas within the body may be avoided. That is, if mechanical force is unintentionally applied to the medical device 100 when the distal end of the medical device 100 is located at a non-target tissue, the medical device 100 is less likely to perforate the non-target tissue.

In some embodiments, the distal tip 403 is substantially bullet-shaped, as shown for example in FIG. 2E, which allows the intended user to drag the distal tip 403 across the surface of tissues in the body of the patient and to catch on to tissues at the target site. For example, if the target site includes a fossa ovalis as described further hereinbelow, the bullet-shaped tip may catch on to the fossa ovalis so that longitudinal force applied at a proximal portion of medical device 100 causes the electrode 106 to advance into and through the fossa ovalis rather than slipping out of the fossa. Because of the tactile feedback provided by the medical device 100, this operation facilitates positioning of the medical device 100 prior to energy delivery to create a channel.

As mentioned hereinabove, in some embodiments, the medical device 100 comprises a hub 108 coupled to the proximal region thereof. In some embodiments, the hub 108 is part of the handle 110 of the medical device 100, facilitates the connection of the elongate member 102 to an energy source, and facilitates the connection of the elongate member 102 to a source of fluid, for example contrast fluid.

Figure 12A:
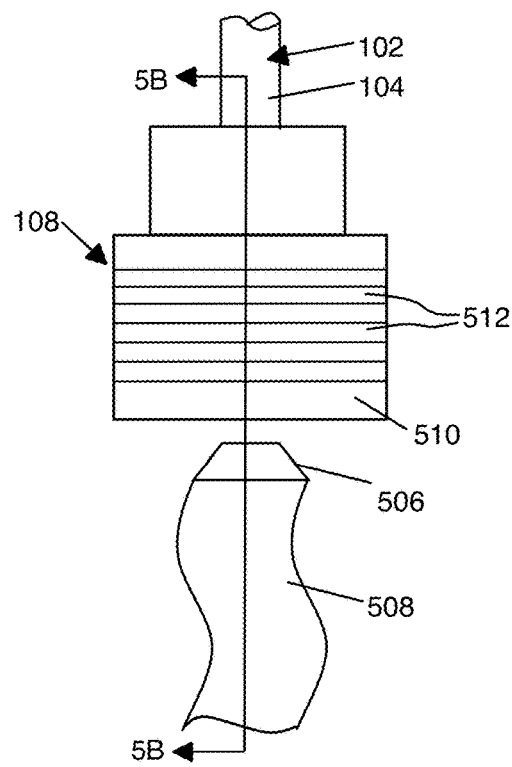
FIG. 12A, in a top elevation view, illustrates an embodiment of a hub.
Figure 12B:
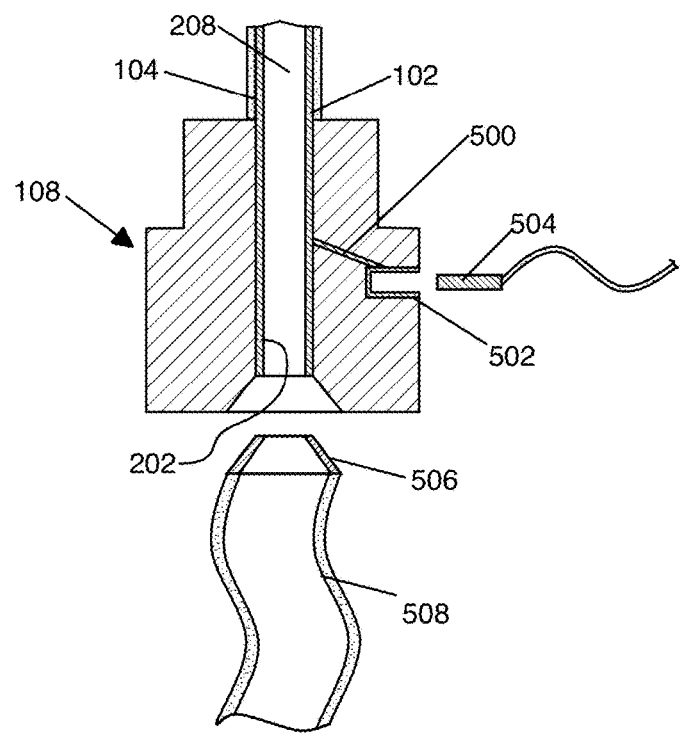
FIG. 12B is a side cross-sectional view taken along the line 5B-5B of FIG. 12A.

In the embodiment illustrated in FIGS. 12A and 12B, the proximal region 200 the of the elongate member 102 is electrically coupled to the hub 108, which is structured to electrically couple the elongate member 102 to a source of energy, for example a radiofrequency generator. For example, in one embodiment, the hub 108 comprises a conductive wire 500, which is connected at one end to the elongate member 102, for example by welding or brazing. The other end of the wire 500 is coupled to a connector, for example a banana jack 502, to which a banana plug 504, electrically coupled to a source of energy, is inserted. Thus, electrical energy may be delivered from the energy source, through plug 504, jack 502 and wire 500 to the elongate member 102 and electrode 106. In other embodiments, other hubs or connectors that allow elongate member 102 to be connected to a source of fluid and a source of energy are used, and the invention is not limited in this regard.

In some embodiments, the hub 108 is structured to be operatively coupled to a connector 506, for example a luer lock, which is connected to tubing 508, and tubing 508 is structured to be operatively coupled at one end thereof to an aspirating device, a source of fluid 712, for example a syringe, or a pressure sensing device, for example a pressure transducer 708. The other end of tubing 508 may be operatively coupled the connector 506, such that tubing 508 and lumen 208 are in fluid communication with each other, thus allowing for a flow of fluid between an external device and the lumen 208.

In some embodiments, the hub 108 further comprises one or more curve direction or orientation indicators 510 that are located on one side of the hub 108 in order to indicate the direction of the curved section 300. The orientation indicator(s) 510 may comprise inks, etching, or other materials that enhance visualization or tactile sensation.

In some embodiments of the invention, the handle 110 includes a relatively large graspable surface so that tactile feedback can be transmitted relatively efficiently, for example by transmitting vibrations. In some embodiments of the invention, the handle 110, for example in the hub 108, includes ridges 512 that enhance this tactile feedback. Indeed, the ridges 512 allow the intended user to fully grasp the handle 110 without holding the handle 110 tightly, which facilitates the transmission of this feedback.

In some embodiments of the invention, the medical device 100, as shown in FIG. 2E, defines a lumen peripheral surface 602 extending substantially peripherally relatively to the end member lumen 216, the lumen peripheral surface 602 being substantially covered with a lumen electrically insulating material 604. This configuration prevents or reduces electrical losses from the lumen peripheral surface 602 to any electrically conducive fluid located within the lumen 208. However, in other embodiments of the invention, the lumen peripheral surface 602 is not substantially covered with the lumen electrically insulating material 604.

Also, in some embodiments of the invention including the curved section 300, the curved section 300 defines a center of curvature (not shown in the drawings) and the side-port(s) 600 extend from the lumen 208 substantially towards the center of curvature. This configuration substantially prevents the edges of the side-port(s) 600 from catching onto tissues as the tissues are perforated. However, in alternative embodiments of the invention, the side-port(s) 600 extend in any other suitable orientation.

In some embodiments, one or more radiopaque markers 714 (as shown in FIG. 8) are associated with the medical device 100 to highlight the location of important landmarks on medical device 100. Such landmarks include the location where the elongate member 102 begins to taper, the location of the electrode 106, or the location of any side-port(s) 600. In some embodiments, the entire distal region 202 of the medical device 100 is radiopaque. This can be achieved by filling the electrical insulator 104, for example Pebax®, with a radiopaque filler, for example Bismuth.

In some embodiments, medical device 100 comprises means for modifying the shape thereof. For example, in some applications, it is desired that medical device 100 be capable of changing between a straight configuration, for example as shown in FIG. 1, and a curved configuration, for example as shown in FIGS. 11A-11C. This may be accomplished by coupling a pull-wire to the medical device 100, such that the distal end of the pull-wire is operatively coupled to the distal region of the medical device 100. When a user applies force to the proximal end of the pull wire, either directly or through an actuating mechanism, the distal region 202 of the medical device 100 is forced to deflect in a particular direction. In other embodiments, other means for modifying the shape of the medical device 100 are used, and the invention is not limited in this regard.

In some embodiments, the medical device 100 includes at least one further electrically conductive component, located proximally relative to the electrode 106, for example, a metal ring positioned on or around the electrical insulator 104 which has a sufficiently large surface area to be operable as a return electrode. In such an embodiment, the medical device 100 may function in a bipolar manner, whereby electrical energy flows from the electrode 106, through tissue at the target site, to the at least one further electrically conductive component. Furthermore, in such embodiments, the medical device 100 includes at least one electrical conductor, for example a wire, for conducting electrical energy from the at least one further conductive component to a current sink, for example circuit ground.

In some embodiments, medical device 100 is used in conjunction with a source of radiofrequency energy suitable for perforating material within a patient's body. The source of energy may be a radiofrequency (RF) electrical generator 700, operable in the range of about 100 kHz to about 1000 kHz, and designed to generate a high voltage over a short period of time. More specifically, in some embodiments, the voltage generated by the generator increases from about 0 V (peak-to-peak) to greater than about 75 V (peak-to-peak) in less than about 0.6 seconds. The maximum voltage generated by generator 700 may be between about 180V peak-to-peak and about 3000V peak-to-peak. The waveform generated may vary, and may include, for example, a sinewave, a rectangular-wave, or a pulsed rectangular wave, amongst others. During delivery of radiofrequency energy, the impedance load may increase due to tissue lesioning near the target-site, or the formation of a vapor layer following cell rupture, for example. In some embodiments, the generator 700 is operable to continue to increase the voltage, even as the impedance load increases. For example, energy may be delivered to a tissue within a body at a voltage that rapidly increases from about 0 V (RMS) to about 220 V (RMS) for a period of between about 0.5 seconds and about 5 seconds.

Without being limited to a particular theory of operation, it is believed that under particular circumstances, as mentioned hereinabove, dielectric breakdown and arcing occur upon the delivery of radiofrequency energy, whereby polar molecules are pulled apart. The combination of these factors may result in the creation of an insulative vapor layer around the electrode, therein resulting in an increase in impedance, for example the impedance may increase to greater than 4000Ω. In some embodiments, despite this high impedance, the voltage continues to increase. Further increasing the voltage increases the intensity of fulguration, which may be desirable as it allows for an increased perforation rate. An example of an appropriate generator for this application is the BMC RF Perforation Generator (model number RFP-100, Baylis Medical Company, Montreal, Canada). This generator delivers continuous RF energy at about 460 kHz.

In some embodiments, a dispersive electrode or grounding pad 702 is electrically coupled to the generator 700 for contacting or attaching to the body of the patient to provide a return path for the RF energy when the generator 700 is operated in a monopolar mode. Alternatively, in embodiments utilizing a bipolar device, for example as described hereinabove, a grounding pad is not necessary as a return path for the RF energy is provided by the further conductive component.

In the embodiment illustrated in FIGS. 12A and 12B, the medical device 100 is operatively coupled to the tubing 508 using connector 506 located at the proximal end of the medical device 100. In some embodiments, the tubing 508 is made of a polymeric material, for example polyvinylchloride (PVC), or another flexible polymer. Some embodiments include the tubing 508 being operatively coupled to an adapter 704, which is structured to provide a flexible region for the user to the handle when releaseably coupling an external pressure transducer, a fluid source or other devices to the adapter. In some embodiments, couplings between elongate member 102, connector 506, and tubing 508, and between tubing 508 and adapter 704, are temporary, for example using Luer locks or other releasable components, and in alternative embodiments, are substantially permanent, for example using an adhesive such as a UV curable adhesive, an epoxy, or another type of bonding agent.

In one broad aspect, the electrosurgical medical device 100 is usable to deliver energy to a target site within a body of a human or animal to perforate or create a void or channel in a material at the target site. Further details regarding delivery of energy to a target site within the body may be found in U.S. patent application Ser. No. 10/347,366 (filed on Jan. 21, 2003), Ser. No. 10/760,749 (filed on Jan. 21, 2004), Ser. No. 10/666,288 (filed on Sep. 19, 2003), and Ser. No. 11/265,304 (filed on Nov. 3, 2005), and U.S. Pat. No. 7,048,733 (application Ser. No. 10/666,301, filed on Sep. 19, 2003) and U.S. Pat. No. 6,565,562 (issued on May 20, 2003), all of which are incorporated herein by reference.

In one specific embodiment, the target site comprises a tissue within the heart of a patient, for example the atrial septum of the heart. In such an embodiment, the target site may be accessed via the inferior vena cava (IVC), for example through the femoral vein.

In one such embodiment, an intended user introduces a guidewire into a femoral vein, typically the right femoral vein, and advances it towards the heart. A guiding sheath, for example a sheath as described in U.S. patent application Ser. No. 10/666,288 (filed on Sep. 19, 2003), previously incorporated herein by reference, is then introduced into the femoral vein over the guidewire, and advanced towards the heart. The distal ends of the guidewire and sheath are then positioned in the superior vena cava. These steps may be performed with the aid of fluoroscopic imaging. When the sheath is in position, a dilator, for example the TorFlex™ Transseptal Dilator of Baylis Medical Company Inc. (Montreal, Canada), or the dilator as described in U.S. patent application Ser. No. 11/727,382 (filed on Mar. 26, 2007), incorporated herein by reference, is introduced into the sheath and over the guidewire, and advanced through the sheath into the superior vena cava. The sheath aids in preventing the dilator from damaging or puncturing vessel walls, for example in embodiments comprising a substantially stiff dilator. Alternatively, the dilator may be fully inserted into the sheath prior to entering the body, and both may be advanced simultaneously towards the heart. When the guidewire, sheath, and dilator have been positioned in the superior vena cava, the guidewire is removed from the body, and the sheath and dilator are retracted slightly, such that they enter the right atrium of the heart. An electrosurgical device, for example medical device 100 described hereinabove, is then introduced into the lumen of the dilator, and advanced toward the heart.

In this embodiment, after inserting the electrosurgical device into the dilator, the user positions the distal end of the dilator against the atrial septum. The electrosurgical device is then positioned such that electrode 106 is aligned with or protruding slightly from the distal end of the dilator. When the electrosurgical device and the dilator have been properly positioned, for example against the fossa ovalis of the atrial septum, a variety of additional steps may be performed, such as measuring one or more properties of the target site, for example an electrogram or ECG (electrocardiogram) tracing and/or a pressure measurement, or delivering material to the target site, for example delivering a contrast agent through side-port(s) 600 and/or open distal end 206. Such steps may facilitate the localization of the electrode 106 at the desired target site. In addition, as mentioned hereinabove, the tactile feedback provided by the proposed medical device 100 is usable to facilitate positioning of the electrode 106 at the desired target site.

With the electrosurgical device and the dilator positioned at the target site, energy is delivered from the energy source, through medical device 100, to the target site. For example, if the medical device 100 is used, energy is delivered through the elongate member 102, to the electrode 106, and into the tissue at the target site. In some embodiments, the energy is delivered at a power of at least about 5 W at a voltage of at least about 75 V (peak-to-peak), and, as described hereinabove, functions to vaporize cells in the vicinity of the electrode, thereby creating a void or perforation through the tissue at the target site. If the heart was approached via the inferior vena cava, as described hereinabove, the user applies force in the substantially cranial direction to the handle 110 of the electrosurgical device as energy is being delivered. The force is then transmitted from the handle to the distal section 112 of the medical device 100, such that the distal section 112 advances at least partially through the perforation. In these embodiments, when the distal section 112 has passed through the target tissue, that is, when it has reached the left atrium, energy delivery is stopped. In some embodiments, the step of delivering energy occurs over a period of between about 1 s and about 5 s.

At this point in the procedure, the diameter of the perforation is typically substantially similar to the outer diameter of the distal section 112. In some examples, the user wishes to enlarge the perforation, such that other devices, for example ablation catheters or other surgical devices, are able to pass therethrough. Typically, to do this, the user applies force to the proximal region of the dilator, for example, in the cranial direction if the heart was approached via the inferior vena cava. The force typically causes the distal end of the dilator to enter the perforation, and pass through the atrial septum. The electrosurgical device is operable to aid in guiding the dilator through the perforation, by acting as a substantially stiff rail for the dilator. In such embodiments, a curve, for example curved section 300 of the medical device 100, typically assists in anchoring the electrosurgical device in the left atrium. In typical embodiments, as force is applied, portions of the dilator of larger diameter pass through the perforation, thereby dilating, expanding, or enlarging the perforation. In some embodiments, the user also applies torque to aid in maneuvering the dilator. Alternatively, in embodiments wherein the device is tapered, for example as described hereinabove, the device may be advanced further into the left atrium, such that larger portions of the device enter and dilate the perforation.

In some embodiments, when the perforation has been dilated to a suitable size, the user stops advancing the dilator. In some such embodiments, a guiding sheath is then advanced over the dilator through the perforation. In alternative embodiments, the sheath is advanced simultaneously with the dilator. At this point in the procedure, the user may retract the dilator and the electrosurgical device proximally through the sheath, leaving only the sheath in place in the heart. The user is then able to perform a surgical procedure on the left side of the heart, via the sheath, for example, introducing a surgical device into the femoral vein through the sheath for performing a surgical procedure to treat electrical or morphological abnormalities within the left side of the heart.

If an apparatus of the present invention, as described hereinabove, is used to carry out a procedure as described herein, then the user is able to maintain the 'feel' of a mechanical perforator, for example a Brockenbrough™ needle, without requiring a sharp tip and large amounts of mechanical force to perforate the atrial septum. Rather, a radiofrequency perforator, for example the electrode 106, is used to create a void or channel through the atrial septum, as described hereinabove, while reducing the risk of accidental puncture of non-target tissues.

In other embodiments, methods of the present invention may be used for treatment procedures involving other regions within the body, and the invention is not limited in this regard. For example, rather than the atrial septum, embodiments of devices, systems and methods of the present invention can be used to treat pulmonary atresia. In some such embodiments, a sheath is introduced into the vascular system of a patient, and guided to the heart, as described hereinabove. A dilator is then introduced into the sheath, and advanced towards the heart, where it is positioned against the pulmonary valve. An electrosurgical device comprising an electrode is then introduced into the proximal region of the dilator, and guided therethrough, such that it is also positioned against the pulmonary valve. Energy is then delivered from the energy source, through the electrode of the electrosurgical device, to the pulmonary valve, such that a puncture or void is created therethrough, as described hereinabove. When the electrosurgical device has passed through the valve, the user is able to apply a force, for example in a substantially cranial direction, to the proximal region of the dilator. The force can be transmitted to the distal region of the dilator, such that the distal region of the dilator enters the puncture and advances through the pulmonary valve. As regions of the dilator of larger diameter pass through the puncture, the puncture or channel becomes dilated.

In other applications, embodiments of a device of the present invention can be used to create voids or channels within or through other tissues of the body, for example within or through the myocardium of the heart. In other embodiments, the device is used to create a channel through a fully or partially occluded lumen within the body. Examples of such lumens include, but are not limited to, blood vessels, the bile duct, airways of the respiratory tract and vessels and/or tubes of the digestive system, the urinary tract and/or the reproductive system. In such embodiments, the device is typically positioned such that an electrode of the device is substantially adjacent the material to be perforated and energy delivered from an energy source, through the electrode 106, to the target site such that a void, puncture, or channel is created in or through the tissue.

This disclosure describes embodiments of a kit and its constituent components which together form an apparatus in which fluid communication between a medical device's lumen and the surrounding environment is provided by a conduit cooperatively defined by the medical device and a tubular member into which the device is inserted. The medical device and tubular member are configured to fit together such that an outer surface of the distal region of the medical device cooperates with an inner surface of the tubular member to define the conduit between the side-port of the medical device and a distal end of the tubular member. The conduit is operable to be used for injecting fluid, withdrawing fluid, and measuring pressure, for example. Methods of assembling and using the apparatus are described as well.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations are apparent to those skilled in the art. Accordingly, it is intended to embrace all such alternatives, modifications and variations that fall within the scope of the appended claims.

We claim:

1. A medical device comprising:
an elongate member having a closed distal end, the elongate member defining a device lumen and at least one side-port in fluid communication with the device lumen, the elongate member defining a proximal portion and a distal portion, the distal portion including the at least one side-port and extending to the closed distal end of the elongate member;
a handle for grasping which is proximal of the proximal portion;
the proximal portion defining a first outer diameter, the distal portion defining a second outer diameter from at least the at least one side-port to an electrode, the first outer diameter being larger than the second outer diameter, and the second outer diameter being substantially constant longitudinally; and
the electrode is at a distal tip of the elongate member for puncturing tissue, the electrode being distal to the at least one side-port.

2. The medical device of claim 1, wherein said elongate member substantially comprises an electrically conductive material, and a layer of insulation covering the electrically conductive material, and the electrode is distal of the layer of insulation.

3. The medical device of claim 1, wherein the electrode defines an exposed surface area and all of the exposed surface area is comprised of an electrically conductive material.

4. The medical device of claim 3, wherein the electrically conductive material comprises a stainless steel.

5. The medical device of claim 1, wherein the device lumen extends past the side-port and has a lumen distal end, wherein the electrode occludes the lumen distal end such that a flow of a fluid in the device lumen is prevented from flowing through the closed distal end of the elongate member.

6. The medical device of claim 5, wherein the elongate member defines a single device lumen.

7. The medical device of claim 1, wherein the elongate member defines a discrete change in diameter between the proximal portion and the distal portion.

8. The medical device of claim 2, wherein the electrically conductive material comprises a metal.

9. The medical device of claim 8, wherein the electrically conductive material defines a metal tube and the layer of insulation covers the metal tube, and the at least one side-port extends through the electrically conductive material defining the metal tube and the layer of insulation which covers the metal tube.

10. A kit comprising:
a tubular member defining a tubular member lumen and a distal end aperture in fluid communication therewith;
a medical device comprising an elongate member having a closed distal end, the elongate member defining a device lumen and at least one side-port in fluid communication with the device lumen, the elongate member defining a proximal portion and a distal portion, distal portion including the at least one side-port and extending to closed distal end of the elongate member,
the medical device having a handle for grasping which is proximal of the proximal portion, and
the proximal portion defining a first outer diameter, the distal portion defining a second outer diameter from at least the at least one side-port to an electrode, the first outer diameter being larger than the second outer diameter, and the second outer diameter being substantially constant longitudinally, and
the electrode is at a distal tip of the elongate member for puncturing tissue, the electrode being distal to the at least one side-port; and
the medical device and tubular member being configured to cooperatively form a conduit between an outer surface of the distal portion and an inner surface of the tubular member when the medical device is inserted within the tubular member lumen, the conduit being formed at least between the side-port and the distal end aperture for enabling fluid communication between the side-port and an environment external to the distal end aperture.

11. The kit of claim 10, wherein the medical device and the tubular member further comprise corresponding markers for aligning the medical device within the tubular member lumen to form said conduit.

12. The kit of claim 11, wherein the corresponding markers are configured for longitudinally aligning the side-port within the tubular member lumen.

13. The kit of claim 11, wherein the corresponding markers are configured for rotationally aligning the side-port within the tubular member lumen.

14. A method comprising the steps of: (a) inserting a medical device into a tubular member wherein the medical device comprises
an elongate member having a closed distal end, the elongate member defining a device lumen and at least one side-port in fluid communication with the device lumen, the elongate member defining a proximal portion and a distal portion, the distal portion including the at least one side-port and extending to the closed distal end of the elongate member;
a handle for grasping which is proximal of the proximal portion;
the proximal portion defining a first outer diameter, the distal portion defining a second outer diameter from at least the at least one side-port to an electrode, the first outer diameter being larger than the second outer diameter, and the second outer diameter being substantially constant longitudinally; and
the electrode is at a distal tip of the elongate member for puncturing tissue, the electrode being distal to the at least one side-port; and
(b) cooperatively defining a conduit for fluid communication by positioning the side-port of the medical device at a location of the tubular member at which a space exists between the side-port and an inner wall of the tubular member, the space forming a part of the conduit, the conduit extending at least between the side-port and a distal end of the tubular member.

15. The method of claim 14, wherein step (b) further comprises aligning the distal tip of the medical device with the distal end of the tubular member.

16. The method of claim 14, wherein step (b) further comprises visualizing at least one marker associated with the medical device, to position the medical device.

17. The method of claim 14, further comprising a step (c) of delivering a fluid through the side-port and distally through the distal end of the tubular member.

18. The method of claim 17, further comprising a step (d) of delivering electrical energy through the medical device to create a puncture through the tissue.

19. The method of claim 18, wherein the tissue comprises a septum of a heart and wherein step (c) comprises staining the septum by delivering contrast fluid through the side-port.

20. The method of claim 14, further comprising a step (c) of measuring a pressure of an environment external to the distal end using the side-port and the conduit.

* * * * *